(12) United States Patent
Ghosh

(10) Patent No.: US 9,877,789 B2
(45) Date of Patent: *Jan. 30, 2018

(54) IMPLANTABLE ELECTRODE LOCATION SELECTION

(71) Applicant: Medtronic, Inc., Minneapolis, MN (US)

(72) Inventor: Subham Ghosh, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 89 days.

This patent is subject to a terminal disclaimer.

(21) Appl. No.: 13/916,353

(22) Filed: Jun. 12, 2013

(65) Prior Publication Data
US 2014/0371832 A1 Dec. 18, 2014

(51) Int. Cl.
*A61B 5/00* (2006.01)
*A61B 19/00* (2006.01)
(Continued)

(52) U.S. Cl.
CPC ............ *A61B 19/50* (2013.01); *A61B 5/0044* (2013.01); *A61B 5/0452* (2013.01); *A61B 5/04085* (2013.01); *A61B 5/489* (2013.01); *A61B 5/6823* (2013.01); *A61B 5/743* (2013.01); *A61B 5/7435* (2013.01); *A61B 6/12* (2013.01); *A61B 6/463* (2013.01); *A61B 6/481* (2013.01); *A61B 6/486* (2013.01); *A61B 6/503* (2013.01); *A61B 6/504* (2013.01); *A61N 1/0484* (2013.01); *A61N 1/368* (2013.01); *A61N 1/3627* (2013.01); *A61N 1/372* (2013.01); *A61N 1/37247* (2013.01); *A61B 5/044* (2013.01); *A61B 5/04012* (2013.01); *A61B 5/0422* (2013.01); *A61B 5/055* (2013.01); *A61B 5/6805* (2013.01); *A61B 5/686* (2013.01);
(Continued)

(58) Field of Classification Search
CPC ..... A61B 5/04012; A61B 5/0452; A61B 5/02; A61B 5/0402; A61B 5/0432; A61B 5/044; A61B 5/742; A61B 6/12; A61B 6/504; A61B 6/466; A61B 6/486; A61B 6/503; A61B 6/507; A61B 6/5217; A61B 6/5235; A61N 1/0484; A61N 1/3684
USPC ........................................................ 607/129
See application file for complete search history.

(56) References Cited

U.S. PATENT DOCUMENTS 4,233,987 A  11/1980 Feingold
4,402,323 A   9/1983 White
(Continued)

FOREIGN PATENT DOCUMENTS

CN  1043621 A  11/1990
CN  1253761 A   5/2000
(Continued)

OTHER PUBLICATIONS

U.S. Appl. No. 13/916,353, filed Jun. 12, 2013, Ghosh.
(Continued)

*Primary Examiner* — Nadia A Mahmood
(74) *Attorney, Agent, or Firm* — Mueting, Raasch & Gebhardt, P.A.

(57) ABSTRACT

Systems, methods, and interfaces are described herein for assisting in noninvasive location selection for an implantable electrode for use in cardiac therapy. Mechanical motion information and surrogate electrical activation times may be used to identify one or more candidate site regions.

37 Claims, 21 Drawing Sheets

(51) Int. Cl.

| | | |
|---|---|---|
| *A61B 6/00* | (2006.01) | |
| *A61N 1/372* | (2006.01) | |
| *A61B 6/12* | (2006.01) | |
| *A61B 5/0408* | (2006.01) | |
| *A61N 1/362* | (2006.01) | |
| *A61N 1/04* | (2006.01) | |
| *A61N 1/368* | (2006.01) | |
| *A61B 5/0452* | (2006.01) | |
| *A61B 5/04* | (2006.01) | |
| *A61B 5/044* | (2006.01) | |
| *A61B 5/042* | (2006.01) | |
| *A61B 5/055* | (2006.01) | |
| *A61B 90/00* | (2016.01) | |

(52) U.S. Cl.
CPC .......... *A61B 6/4405* (2013.01); *A61B 6/4441* (2013.01); *A61B 2090/3966* (2016.02); *A61B 2562/043* (2013.01); *A61B 2562/046* (2013.01); *A61B 2576/023* (2013.01)

(56) References Cited

U.S. PATENT DOCUMENTS

| | | | |
|---|---|---|---|
| 4,428,378 A | 1/1984 | Anderson et al. | |
| 4,497,326 A | 2/1985 | Curry | |
| 4,566,456 A | 1/1986 | Koning et al. | |
| 4,593,702 A | 6/1986 | Kepski | |
| 4,674,511 A | 6/1987 | Cartmell | |
| 4,763,660 A | 8/1988 | Kroll et al. | |
| 4,777,955 A | 10/1988 | Brayten et al. | |
| 4,787,389 A | 11/1988 | Tarjan | |
| 4,979,507 A | 12/1990 | Heinz et al. | |
| 5,052,388 A | 10/1991 | Sivula et al. | |
| 5,054,496 A | 10/1991 | Wen et al. | |
| 5,311,873 A | 5/1994 | Savard et al. | |
| 5,331,960 A | 7/1994 | Lavine | |
| 5,334,220 A | 8/1994 | Sholder | |
| 5,443,492 A | 8/1995 | Stokes et al. | |
| 5,485,849 A | 1/1996 | Panescu et al. | |
| 5,514,163 A | 5/1996 | Markowitz et al. | |
| 5,552,645 A | 9/1996 | Weng | |
| 5,628,778 A | 5/1997 | Kruse et al. | |
| 5,671,752 A | 9/1997 | Sinderby et al. | |
| 5,683,429 A | 11/1997 | Mehra | |
| 5,683,432 A | 11/1997 | Goedeke et al. | |
| 5,687,737 A | 11/1997 | Branham et al. | |
| 5,810,740 A | 9/1998 | Paisner | |
| 5,876,336 A | 3/1999 | Swanson et al. | |
| 5,891,045 A | 4/1999 | Albrecht et al. | |
| 5,922,014 A | 7/1999 | Warman et al. | |
| 6,055,448 A | 4/2000 | Anderson et al. | |
| 6,128,535 A | 10/2000 | Maarse et al. | |
| 6,141,588 A | 10/2000 | Cox et al. | |
| 6,187,032 B1 | 2/2001 | Ohyu et al. | |
| 6,205,357 B1 | 3/2001 | Ideker et al. | |
| 6,226,542 B1 | 5/2001 | Reisfeld | |
| 6,236,883 B1 | 5/2001 | Ciaccio et al. | |
| 6,243,603 B1 | 6/2001 | Ideker et al. | |
| 6,246,898 B1 | 6/2001 | Vesely et al. | |
| 6,301,496 B1 | 10/2001 | Reisfeld | |
| 6,311,089 B1 | 10/2001 | Mann et al. | |
| 6,330,476 B1 | 12/2001 | Ben-Haim et al. | |
| 6,358,214 B1 | 3/2002 | Tereschouk | |
| 6,377,856 B1 | 4/2002 | Carson | |
| 6,381,493 B1 | 4/2002 | Stadler et al. | |
| 6,393,316 B1 | 5/2002 | Gillberg et al. | |
| 6,418,346 B1 | 7/2002 | Nelson et al. | |
| 6,442,433 B1 | 8/2002 | Linberg | |
| 6,456,867 B2 | 9/2002 | Reisfeld | |
| 6,473,638 B2 | 10/2002 | Ferek-Petric | |
| 6,480,745 B2 | 11/2002 | Nelson et al. | |
| 6,484,118 B1 | 11/2002 | Govari | |
| 6,507,756 B1 | 1/2003 | Heynen et al. | |
| 6,532,379 B2 | 3/2003 | Stratbucker | |
| 6,584,343 B1 | 6/2003 | Ransbury et al. | |
| 6,599,250 B2 | 7/2003 | Webb et al. | |
| 6,625,482 B1 | 9/2003 | Panescu et al. | |
| 6,640,136 B1 | 10/2003 | Helland et al. | |
| 6,650,927 B1 | 11/2003 | Keidar | |
| 6,766,189 B2 | 7/2004 | Yu et al. | |
| 6,772,004 B2 | 8/2004 | Rudy | |
| 6,804,555 B2 | 10/2004 | Warkentin | |
| 6,847,836 B1 | 1/2005 | Sujdak | |
| 6,856,830 B2 | 2/2005 | He | |
| 6,882,882 B2 | 4/2005 | Struble et al. | |
| 6,885,889 B2 | 4/2005 | Chinchoy | |
| 6,915,149 B2 | 7/2005 | Ben-Haim | |
| 6,968,237 B2 | 11/2005 | Doan et al. | |
| 6,975,900 B2 | 12/2005 | Rudy et al. | |
| 6,978,184 B1 | 12/2005 | Marcus et al. | |
| 6,980,675 B2 | 12/2005 | Evron et al. | |
| 7,016,719 B2 | 3/2006 | Rudy et al. | |
| 7,031,777 B2 | 4/2006 | Hine et al. | |
| 7,058,443 B2 | 6/2006 | Struble | |
| 7,062,315 B2 | 6/2006 | Koyrakh et al. | |
| 7,092,759 B2 | 8/2006 | Nehls et al. | |
| 7,142,922 B2 | 11/2006 | Spinelli et al. | |
| 7,184,835 B2 | 2/2007 | Kramer et al. | |
| 7,215,998 B2 | 5/2007 | Wesselink et al. | |
| 7,286,866 B2 | 10/2007 | Okerlund et al. | |
| 7,308,297 B2 | 12/2007 | Reddy et al. | |
| 7,308,299 B2 | 12/2007 | Burrell et al. | |
| 7,313,444 B2 | 12/2007 | Pianca et al. | |
| 7,321,677 B2 | 1/2008 | Evron et al. | |
| 7,346,381 B2 | 3/2008 | Okerlund et al. | |
| 7,398,116 B2 | 7/2008 | Edwards | |
| 7,426,412 B1 | 9/2008 | Schecter | |
| 7,454,248 B2 | 11/2008 | Burrell et al. | |
| 7,499,743 B2 | 3/2009 | Vass et al. | |
| 7,509,170 B2 | 3/2009 | Zhang et al. | |
| 7,565,190 B2 | 7/2009 | Okerlund et al. | |
| 7,587,074 B2 | 9/2009 | Zarkh et al. | |
| 7,599,730 B2 | 10/2009 | Hunter et al. | |
| 7,610,088 B2 | 10/2009 | Chinchoy | |
| 7,613,500 B2 | 11/2009 | Vass et al. | |
| 7,616,993 B2 | 11/2009 | Müssig et al. | |
| 7,664,550 B2 | 2/2010 | Eick et al. | |
| 7,684,863 B2 | 3/2010 | Parikh et al. | |
| 7,742,629 B2 | 6/2010 | Zarkh et al. | |
| 7,747,047 B2 | 6/2010 | Okerlund et al. | |
| 7,751,882 B1 | 7/2010 | Helland et al. | |
| 7,769,451 B2 | 8/2010 | Yang et al. | |
| 7,778,685 B2 | 8/2010 | Evron et al. | |
| 7,778,686 B2 | 8/2010 | Vass et al. | |
| 7,787,951 B1 | 8/2010 | Min | |
| 7,813,785 B2 | 10/2010 | Okerlund et al. | |
| 7,818,040 B2 | 10/2010 | Spear et al. | |
| 7,848,807 B2 | 12/2010 | Wang | |
| 7,860,580 B2 | 12/2010 | Falk et al. | |
| 7,894,889 B2 | 2/2011 | Zhang | |
| 7,912,544 B1 | 3/2011 | Min et al. | |
| 7,917,214 B1 | 3/2011 | Gill et al. | |
| 7,941,213 B2 | 5/2011 | Markowitz et al. | |
| 7,953,475 B2 | 5/2011 | Harley et al. | |
| 7,953,482 B2 | 5/2011 | Hess | |
| 7,983,743 B2 | 7/2011 | Rudy et al. | |
| 7,996,063 B2 | 8/2011 | Vass et al. | |
| 7,996,070 B2 | 8/2011 | van Dam et al. | |
| 8,010,194 B2 | 8/2011 | Muller | |
| 8,019,402 B1 | 9/2011 | Kryzpow et al. | |
| 8,019,409 B2 | 9/2011 | Rosenberg et al. | |
| 8,032,229 B2 | 10/2011 | Gerber et al. | |
| 8,036,743 B2 | 10/2011 | Savage et al. | |
| 8,060,185 B2 | 11/2011 | Hunter et al. | |
| 8,150,513 B2 | 4/2012 | Chinchoy | |
| 8,160,700 B1 | 4/2012 | Ryu et al. | |
| 8,175,703 B2 | 5/2012 | Dong et al. | |
| 8,180,428 B2 | 5/2012 | Kaiser et al. | |
| 8,195,292 B2 | 6/2012 | Rosenberg et al. | |
| 8,213,693 B1 | 7/2012 | Li | |
| 8,214,041 B2 | 7/2012 | Van Gelder et al. | |
| 8,265,738 B1 | 9/2012 | Min et al. | |
| 8,285,377 B2 | 10/2012 | Rosenberg et al. | |

(56) References Cited

U.S. PATENT DOCUMENTS

| | | |
|---|---|---|
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1* | 8/2009 | Assis ............... A61B 6/12 600/424 |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1* | 11/2012 | Gosh ............... A61B 5/0402 600/510 |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |

(56) References Cited

U.S. PATENT DOCUMENTS

| | | | |
|---|---|---|---|
| 2013/0116739 A1* | 5/2013 | Brada | A61B 6/486 607/9 |
| 2013/0131529 A1* | 5/2013 | Jia | A61B 5/04012 600/510 |
| 2013/0131749 A1 | 5/2013 | Sheldon et al. | |
| 2013/0131751 A1 | 5/2013 | Stadler et al. | |
| 2013/0136035 A1 | 5/2013 | Bange et al. | |
| 2013/0150913 A1 | 6/2013 | Bornzin et al. | |
| 2013/0165983 A1 | 6/2013 | Ghosh et al. | |
| 2013/0165988 A1 | 6/2013 | Ghosh | |
| 2013/0261471 A1 | 10/2013 | Saha et al. | |
| 2013/0261688 A1 | 10/2013 | Dong et al. | |
| 2013/0289640 A1 | 10/2013 | Zhang et al. | |
| 2013/0296726 A1 | 11/2013 | Niebauer et al. | |
| 2013/0304407 A1 | 11/2013 | George et al. | |
| 2013/0324828 A1 | 12/2013 | Nishiwaki et al. | |
| 2014/0005563 A1 | 1/2014 | Ramanathan et al. | |
| 2014/0018872 A1 | 1/2014 | Siejko et al. | |
| 2014/0135866 A1 | 5/2014 | Ramanathan et al. | |
| 2014/0135867 A1 | 5/2014 | Demmer et al. | |
| 2014/0163633 A1 | 6/2014 | Ghosh et al. | |
| 2014/0222099 A1 | 8/2014 | Sweeney | |
| 2014/0236252 A1 | 8/2014 | Ghosh et al. | |
| 2014/0276125 A1 | 9/2014 | Hou et al. | |
| 2014/0277233 A1 | 9/2014 | Ghosh | |
| 2014/0323882 A1 | 10/2014 | Ghosh et al. | |
| 2014/0323892 A1 | 10/2014 | Ghosh et al. | |
| 2014/0323893 A1 | 10/2014 | Ghosh et al. | |
| 2014/0371807 A1 | 12/2014 | Ghosh et al. | |
| 2014/0371808 A1 | 12/2014 | Ghosh et al. | |
| 2014/0371833 A1 | 12/2014 | Ghosh et al. | |
| 2015/0032016 A1 | 1/2015 | Ghosh | |
| 2015/0032171 A1 | 1/2015 | Ghosh | |
| 2015/0032172 A1 | 1/2015 | Ghosh | |
| 2015/0032173 A1 | 1/2015 | Ghosh | |
| 2015/0045849 A1 | 2/2015 | Ghosh et al. | |
| 2015/0142069 A1 | 5/2015 | Sambelashvili | |
| 2015/0157225 A1 | 6/2015 | Gillberg et al. | |
| 2015/0157231 A1 | 6/2015 | Gillberg et al. | |
| 2015/0157232 A1 | 6/2015 | Gillberg et al. | |
| 2015/0157865 A1 | 6/2015 | Gillberg et al. | |
| 2015/0216434 A1 | 8/2015 | Ghosh et al. | |
| 2015/0265840 A1 | 9/2015 | Ghosh et al. | |
| 2016/0030747 A1 | 2/2016 | Thakur et al. | |
| 2016/0030751 A1 | 2/2016 | Ghosh et al. | |
| 2016/0045737 A1 | 2/2016 | Ghosh et al. | |
| 2016/0045738 A1 | 2/2016 | Ghosh et al. | |
| 2016/0045744 A1 | 2/2016 | Ghosh et al. | |
| 2016/0184590 A1 | 6/2016 | Gosh | |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 98/26712 A1 | 6/1998 |
| WO | WO 1999/006112 A1 | 2/1999 |
| WO | WO 00/45700 | 8/2000 |
| WO | WO 01/67950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | PCT/US2014/036153 | 4/2014 |
| WO | PCT/US2014/036163 | 4/2014 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

U.S. Appl. No. 13/916,377, filed Jun. 12, 2013, Ghosh.
U.S. Appl. No. 13/952,043, filed Jul. 26, 2013, Ghosh.
U.S. Appl. No. 13/952,061, filed Jul. 26, 2013, Ghosh.
U.S. Appl. No. 14/190,508, filed Feb. 26, 2014.
U.S. Appl. No. 14/190,578, filed Feb. 26, 2014.
U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/227,919, filed Mar. 27, 2014, Ghosh et al.
U.S. Appl. No. 14/227,955, filed Mar. 27, 2014, Ghosh et al.
U.S. Appl. No. 14/227,962, filed Mar. 27, 2014, Ghosh et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.
International Search Report and Written Opinion for PCT/US2014/036262, dated May 3, 2012; 9 pg.
International Search Report and Written Opinion for PCT/US2014/036302, dated May 3, 2012; 9 pg.
"CardioGuide System Enables Real-Time Navigation of Left Ventricular Leads During Medtronic CRT Implants," Press Release, Apr. 9, 2013, Medtronic, Inc., 2 pgs.
Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

(56) References Cited

OTHER PUBLICATIONS

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.

Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

"Heart Failure Management" datasheet [online]. Medtronic, Minneapolis, Minnesota, [Last updated on Jun. 3, 2013].Retrieved from the Internet: www.medtronic.com; 9 pages.

Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of St Segment Changes in Acute Myocardial Infarction," *Circulation*, 1993; 87: 773-782.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.

Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.

Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms : a simulation study," Circulation Research, 1989, 64:449-462.

Sweeney et al., "Analysis of Ventricular Activation Using Surface Electrocardiography to Predict Left Ventricular Reverse Volumetric Remoldeling During Cardiac Resynchronization Therapy," *Circulation*, Feb. 9, 2010; 121(5):626-34. Available online Jan. 25, 2010.

Turner et al, "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Varma et al., "Placebo CRT," *Journal of Cardiovascular Electrophysiology*, vol. 19, Aug. 2008; p. 878.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

International Search Report and Written Opinion dated Mar. 9, 2015, for International Application No. PCT/US2014/069214.

International Search Report and Written Opinion dated Mar. 17, 2015, for International Application No. PCT/US2014/069192.

International Search Report and Written Opinion dated Mar. 16, 2015, for International Application No. PCT/US2014/069182.

International Search Report / Written Opinion, dated Aug. 6, 2014; Patent Application No. PCT/US2014/036153, filed Apr. 30, 2014; 14 pages.

International Search Report / Written Opinion, dated Nov. 7, 2014; Patent Application No. PCT/US2014/036163, filed Apr. 30, 2014; 12 pages.

international Search Report / Written Opinion, dated Oct. 28, 2014; Patent Application No. PCT/US2014/041928, filed Jun. 11, 2014; 15 pages.

International Search Report / Written Opinion, dated Oct. 24. 2014; Patent Application No. PCT/US2014/041929, filed Jun. 11, 2014, 15 pages.

U.S. Appl. No. 14/173,288, filed Feb. 5, 2014, Sambelashvili.

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

Hayes et al., "Cardiac Resynchronization Therapy and the Relationship of Percent Biventricular Pacing to Symptoms and Survival," *Heart Rhythm*, Sep. 2011; 8(9):1469-1475.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

International Search Report and Written Opinion dated May 3, 2012 for International Application No. PCT/US2012/036262; 9 pages.

International Search Report and Written Opinion dated May 3, 2012 for International Application No. PCT/US2012/036302; 9 pages.

International Search Report and Written Opinion dated Apr. 8, 2015, for International Application No. PCT/US2014/069070; 11 pages.

International Search Report and Written Opinion for PCT/US2014/0247583, dated Nov. 4, 2014; 7 pages.

International Search Report and Written Opinion dated Nov. 12, 2014 for International Application No. PCT/US2014/047971; 7 pages.

International Search Report and Written Opinion dated Nov. 12, 2014 for International Application No. PCT/US2014/048120; 7 pages.

International Search Report and Written Opinion dated Jun. 11, 2015 for International Application No. PCT/US2015/021442; 13 pages.

Cuculich et al., "The Electrophysiological Cardiac Ventricular Substrate in Patients After Myocardial Infarction," *J. Am. Coll. Cardiol.*, 2011; 58:1893-1902.

Dawoud et al., "Inverse Electrocardiographic Imaging to Assess Electrical Dyssynchrony in Cardiac Resynchronization Therapy Patients," *Computing in Cardiology*, 2012; 39:993-996.

Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.

Medtronic Vitatron Carelink Encore® Programmer Model 29901 Reference Manual, 2013, Medtronic, Inc., Minneapolis, MN.

Potse et al., "Mathematical Modeling and Simulation of Ventricular Activation Sequences: Implications for Cardiac Resynchronization Therapy," *J. of Cardiovasc. Trans. Res.*, 2012; 5:146-158.

Prinzen et al., "Cardiac Resynchronization Therapy State-of-the-Art of Current Applications, Guidelines, Ongoing Trials, and Areas of Controversy" *Circulation*, 2013; 128: 2407-2418.

Strik et al., "Electrical and Mechanical Ventricular Activation During Left Bundle Branch Block and Resynchronization," *J. of Cardiovasc. Trans. Res.*, 2012; 5:11-126.

Miri et al., "Applicability of body surface potential map in computerized optimization of biventricular pacing," *Annals of Biomedical Engineering*, vol. 38, No. 3, Mar. 2010, pp. 865-875.

Miri et al., "Comparison of the electrophysiologically based optimization methods with different pacing parameters in patient undergoing resynchronization treatment," *30th Annual International IEEE EMS Conference*, Aug. 2008, pp. 1741-1744.

Miri et al., "Computerized Optimization of Biventricular Pacing Using Body Surface Potential Map," *31st Annual International Conference of the IEEE EMBS*, Sep. 2009, pp. 2815-2818.

(56) References Cited

OTHER PUBLICATIONS

Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.

Svendsen et al., "Computational Models of Cardiac Electrical Activation," Chapter 5, Computational Nov. 2010, pp. 73-88.

Wang et al., "Application of the Method of Fundamental Solutions to Potential-based Inverse Electrocardiography," *Annals of Biomedical Engineering*, Aug. 2006, pp. 1272-1288.

Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.

Fung et al., Chapter 20, Optimization of Cardiac Resynchronization Therapy, Cardiac Resynchronization Therapy, Second Edition, Copyright 2008, Blackwell Publishing Ltd., pp. 356-373.

Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.

Nash et al., "An Experimental-Computational Framework for Validating in-vivo ECG Inverse Algorithms," International Journal of Bioelectromagnetism, vol. 2, No. 2, Dec. 31, 2000, 9 pp.

Sweeney et al., QRS Fusion Complex Analysis Using Wave Interference to Predict Reverse Remodeling During Cardiac Resynchronization Therapy, heart Rhythm, 2014, 11:806-813.

Wellens, MD et al., "The Electrocardiogram 102 Years After Einthoven," Circulation, Feb. 2004; vol. 109, No. 5, pp. 562-564.

\* cited by examiner

FIG. 4
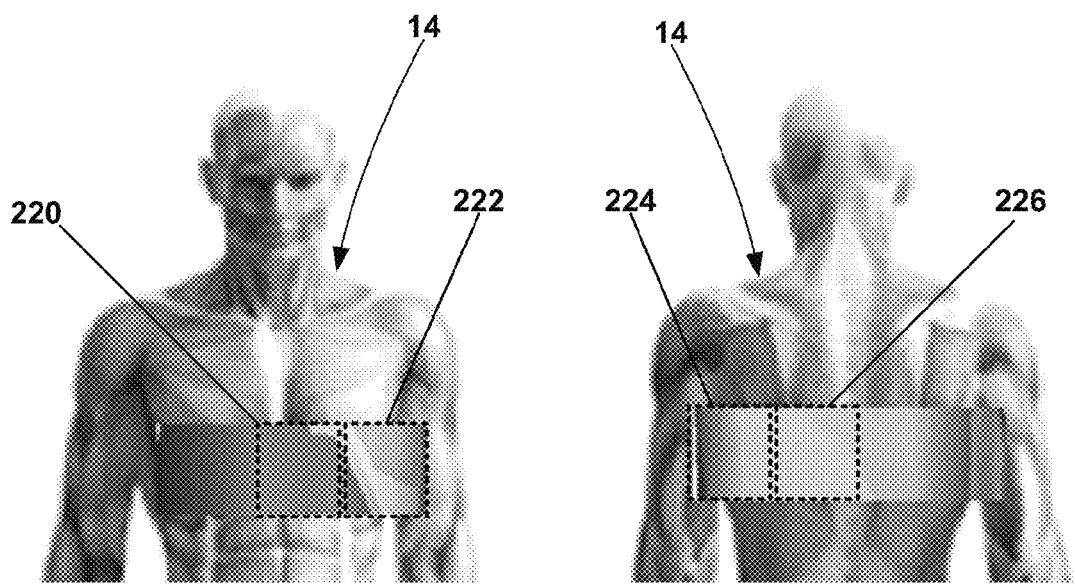
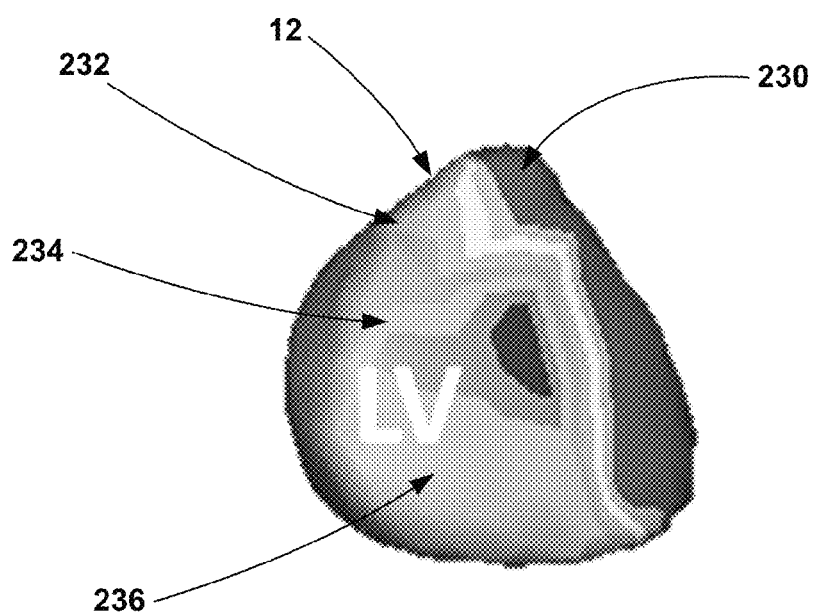

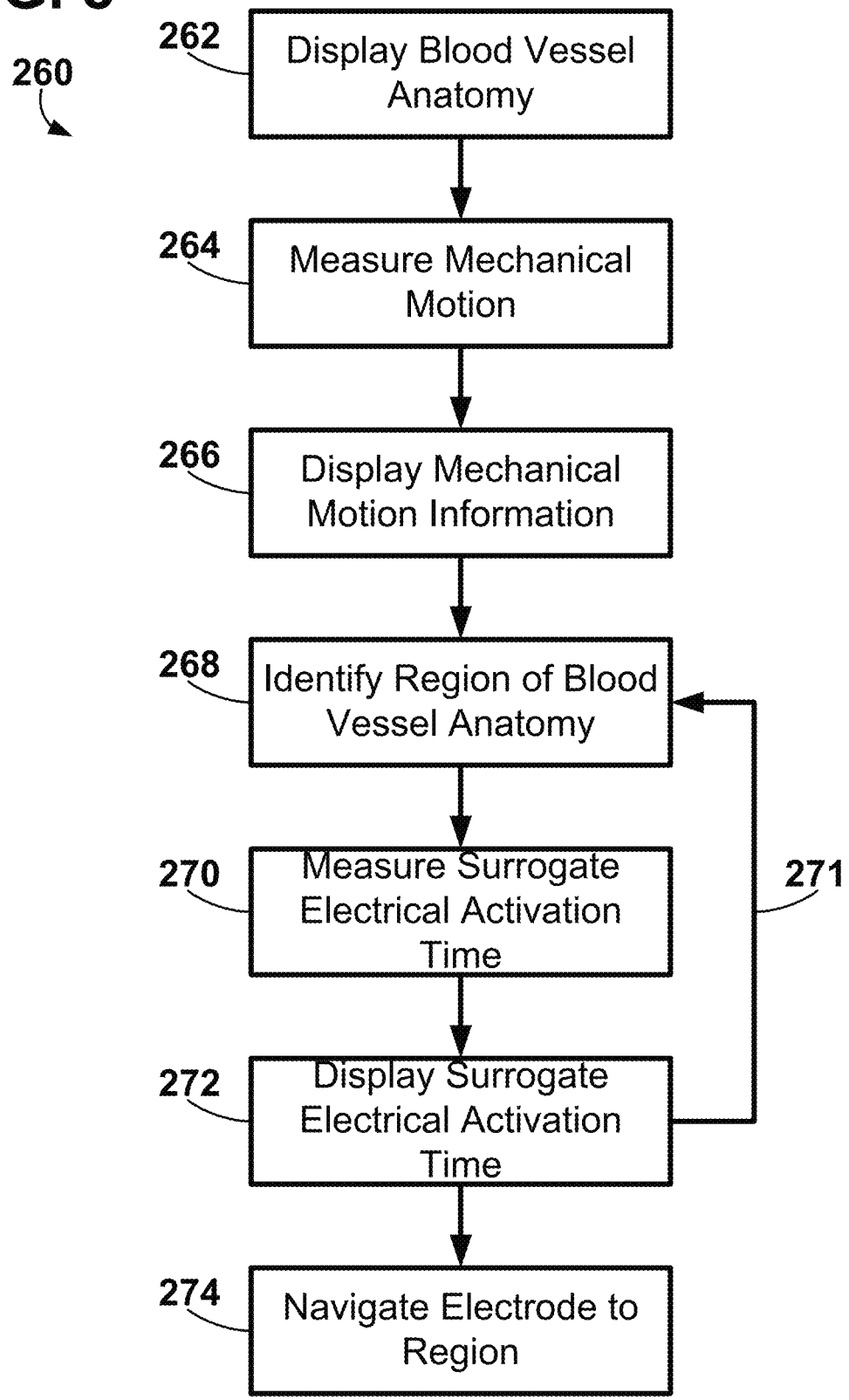

IMPLANTABLE ELECTRODE LOCATION SELECTION

The disclosure herein relates to systems, methods, and interfaces for implantable electrode location selection.

Implantable electrodes may be used in various systems, apparatus, and methods for medical treatment of a patient. More specifically, implantable electrodes may be located adjacent, or in contact, with tissue (e.g., cardiac tissue, etc.) of a patient to deliver therapy to the tissue of the patient and/or sense signals from the tissue of the patient. Some electrodes may be more effective, or optimal, at delivering therapy than others (e.g., due to location, contact, etc.).

Various pacing therapies (e.g., cardiac resynchronization therapy) may deliver electrical pacing to the left ventricle of a patient's heart. Implantable electrodes used to deliver left ventricular pacing may be located in one or more branches of the coronary sinus proximate the patient's left ventricle. Different implantation site regions (e.g., locations within the one or more branches) of the coronary sinus may be more effective, or optimal, than others in delivering pacing therapy.

SUMMARY

The exemplary systems, methods, and interfaces described herein may be configured to assistance a user (e.g., a physician) in the location selection for one or more implantable electrodes for use in delivering cardiac therapy to a patient. The systems, methods, and interfaces may be described as being non-invasive. For example, the systems, methods, and interfaces may not use implantable devices such as leads, probes, catheters, etc. to assist the user in the location selection for one or more implantable electrodes. Further, for example, the systems, methods, and interfaces may not relate to feedback from what occurs during pacing from a given location of an implanted electrode. In other words, the exemplary systems, methods, and interfaces may be directed to selecting an optimal implantable electrode position before the implanted electrode is implanted, or put into, a patient from electrical and/or mechanical measurements taken noninvasively.

More specifically, the exemplary systems, methods, and interfaces may use mechanical motion data in combination with surrogate electrical activation data to identify one or more candidate and/or target implant site regions for the implantable electrodes. The mechanical motion data may be measured using imaging apparatus configured to image at least a portion of a patients heart (e.g., a portion of the heart's blood vessel anatomy). The surrogate electrical activation data may be measured using one or more external electrodes (e.g., external to a patient's body) located adjacent a patient's skin. In at least one embodiment, the surrogate electrical activation data may be noninvasive estimations of local activation times (e.g., q-LV times) of regions of a patient's heart taken along the short-axis of the heart (e.g., electrical activation times may not vary much across the long-axis of the heart).

Additionally, one or more graphical user interfaces may display mechanical motion information and/or surrogate electrical activation information of a patient to, e.g., assist a user in the selection of locations for one or more implantable electrodes, and subsequently, navigating the one or more implantable electrodes to such locations. The exemplary systems, methods, and interfaces may be described as a tool to provide additional information to a user to aid in the location selection for implantable electrodes and/or an automated recommendation engine to identify locations for one or more implantable electrodes.

One exemplary system for assisting in noninvasive location selection for an implantable electrode may include electrode apparatus, imaging apparatus, display apparatus, and computing apparatus coupled to the electrode apparatus, imaging apparatus, and display apparatus. The electrode apparatus may include a plurality of external electrodes configured to be located proximate tissue of a patient (e.g., surface electrodes positioned in an array configured to be located proximate the skin of the patient). The imaging apparatus may be configured to image at least a portion of blood vessel anatomy of the patient's heart (e.g., at least a portion of the coronary sinus). The display apparatus may include a graphical user interface configured to depict the at least a portion of blood vessel anatomy of the patient's heart for implantation of an implantable electrode. The computing apparatus may be configured to assist a user in noninvasively selecting a location for the implantable electrode. The computing apparatus may be further configured to measure mechanical motion of a plurality of implantation site regions of the at least a portion of blood vessel anatomy of the patient's heart using the imaging apparatus, wherein each region of the plurality of implantation site regions is different from the other regions of the plurality of implantation site regions and measure surrogate electrical activation time of the plurality of implantation site regions of the patient's heart using the plurality of external electrodes of the electrode apparatus. The surrogate electrical activation time for each region of the plurality of implantation site regions may be measured using one or more external electrodes. The computing apparatus may be further configured to determine one or more candidate site regions of the plurality of implantation site regions of the at least a portion of blood vessel anatomy of the patient's heart for implantation of the implantable electrode based on the measured mechanical motion and measured electrical activation time of the plurality of regions. The one or more candidate site regions may include mechanical motion contraction times greater than or equal to a mechanical motion threshold based on the latest mechanical motion contraction time of the plurality of implantation site regions and electrical activation times greater than or equal to an electrical activation threshold based on the latest electrical activation time of the plurality of implantation site regions (e.g., the mechanical motion threshold may be a selected percentage of the latest mechanical motion contraction time of the plurality of implantation site regions and the electrical activation threshold may be a selected percentage of the latest electrical activation time of the plurality of implantation site regions). The computing apparatus may be further configured to identify, on the graphical user interface, the one or more candidate site regions for implantation of the implantable electrode.

One exemplary method for assisting in noninvasive location selection for an implantable electrode may include measuring mechanical motion of a plurality of implantation site regions of at least a portion of blood vessel anatomy of the patient's heart (e.g., at least a portion of the coronary sinus) using imaging apparatus. Each region of the plurality of implantation site regions may be different from the other regions of the plurality of implantation site regions. The exemplary method may further include measuring surrogate electrical activation time of the plurality of implantation site regions of the patient's heart using a plurality of external electrodes. The surrogate electrical activation time for each region of the plurality of implantation site regions may be measured using one or more external electrodes (e.g., surface electrodes positioned in an array configured to be located proximate the skin of the patient). The exemplary method may include determining one or more candidate site regions of the plurality of implantation site regions of the at least a portion of blood vessel anatomy of the patient's heart for implantation of an implantable electrode based on the measured mechanical motion and measured electrical activation time of the plurality of regions. The one or more candidate site regions may include mechanical motion contraction times greater than or equal to a mechanical motion threshold based on the latest mechanical motion contraction time of the plurality of implantation site regions and electrical activation times greater than or equal to an electrical activation threshold based on the latest electrical activation time of the plurality of implantation site regions (e.g., the mechanical motion threshold may be a selected percentage of the latest mechanical motion contraction time of the plurality of implantation site regions and the electrical activation threshold may be a selected percentage of the latest electrical activation time of the plurality of implantation site regions). The exemplary method may include identifying, on a graphical user interface, the one or more candidate site regions for implantation of the implantable electrode and navigating at least one implantable electrode to at least one of the identified one or more candidate site regions using the graphical user interface.

In one or more exemplary systems and/or methods, measuring surrogate electrical activation time of the plurality of implantation site regions of the patient's heart using the plurality of external electrodes may include measuring surrogate electrical activation time of each implantation site region using one or more external electrodes proximate thereto.

In one or more exemplary systems and/or methods, measuring surrogate electrical activation time of the plurality of implantation site regions of the patient's heart using the plurality of external electrodes may include determining positions of the plurality of external electrodes with respect to the plurality regions of the at least a portion of blood vessel anatomy of the patient's heart using the imaging apparatus, associating one or more external electrodes with each region of the plurality of regions of the at least a portion of blood vessel anatomy of the patient's heart, and measuring surrogate electrical activation time of each region of the plurality of regions of the at least a portion of blood vessel anatomy of the patient's heart using the one or more external electrodes associated therewith.

In one or more exemplary systems and/or methods, one or more external electrodes of the plurality of external electrodes may be associated with each region of the plurality of implantation site regions, measuring surrogate electrical activation time of the plurality of implantation site regions of the patient's heart using the plurality of external electrodes may include positioning the plurality of external electrodes proximate tissue of the patient (e.g., where the one or more external electrodes associated with each region of the plurality of implantation site regions are positioned proximate an area of the patient associated with the respective region of the plurality of implantation site regions), and measuring surrogate electrical activation time of the plurality of regions of the patient's heart using the plurality of electrodes of the electrode apparatus may include measuring surrogate electrical activation time of each region of the plurality of regions of the at least a portion of blood vessel anatomy of the patient's heart using the one or more external electrodes associated therewith.

In one or more exemplary systems and/or methods, the computing apparatus may be further configured to execute or the method may further include determining a scar risk score for each region of the one or more candidate site regions, identifying, on the graphical user interface, at least one target site region of the one or more candidate site regions based on the scar risk score for implantation of the implantable electrode, and navigating at least one implantable electrode to the at least one identified target site regions using the graphical user interface. The scar risk score may be based on at least one of peak-to-peak amplitude of measured mechanical motion of the candidate site region, fractionations of the electrical activity of the candidate site region measured using the one or more electrodes used to measure the surrogate electrical activation time therefor, ST segment elevation of the electrical activity of the candidate site region measured using the one or more electrodes used to measure the surrogate electrical activation time therefor, and low peak-to-peak amplitude of the electrical activity of the candidate site region measured using the one or more electrodes used to measure the surrogate electrical activation time therefor.

One exemplary system for assisting in noninvasive location selection for an implantable electrode may include electrode apparatus, imaging apparatus, display apparatus, and computing apparatus coupled to the electrode apparatus, imaging apparatus, and display apparatus. The electrode apparatus may include a plurality of external electrodes configured to be located proximate tissue of a patient and the imaging apparatus configured to image at least a portion of blood vessel anatomy of the patient's heart. The display apparatus may include a graphical user interface configured to depict the at least a portion of blood vessel anatomy of the patient's heart for implantation of an implantable electrode. The computing apparatus may be configured to assist a user in noninvasively selecting a location for the implantable electrode. The computing apparatus may be further configured to measure mechanical motion of a plurality of implantation site regions of the at least a portion of blood vessel anatomy of the patient's heart using the imaging apparatus (e.g., where each region of the plurality of implantation site regions is different from the other regions of the plurality of implantation site regions), measure surrogate electrical activation time of the plurality of implantation site regions of the patient's heart using the plurality of external electrodes of the electrode apparatus (e.g., where the surrogate electrical activation time for each region of the plurality of implantation site regions is measured using one or more external electrodes), and determine one or more candidate site regions of the plurality of implantation site regions of the at least a portion of blood vessel anatomy of the patient's heart for implantation of the implantable electrode based on the measured mechanical motion and measured electrical activation time of the plurality of regions.

One exemplary method for assisting in noninvasive location selection for an implantable electrode may include measuring mechanical motion of a plurality of implantation site regions of at least a portion of blood vessel anatomy of the patient's heart using imaging apparatus where each region of the plurality of implantation site regions is different from the other regions of the plurality of implantation site regions and measuring surrogate electrical activation time of the plurality of implantation site regions of the patient's heart using a plurality of external electrodes where the surrogate electrical activation time for each region of the plurality of implantation site regions is measured using one or more external electrodes. The exemplary method may further include determining one or more candidate site regions of the plurality of implantation site regions of the at least a portion of blood vessel anatomy of the patient's heart for implantation of an implantable electrode based on the measured mechanical motion and measured surrogate electrical activation time of the plurality of regions.

One exemplary noninvasive method may include identifying areas of late electrical activation based on surface ECG leads in a proprietary 'belt-like' configuration. Sequence of ventricular activation during intrinsic rhythm and/or right ventricular pacing may be derived from this belt. Regions of the late left ventricle activation can be determined from the derived sequence. The data can be used in conjunction with data derived from mechanical motion of the left-ventricle (e.g., motion maps) to pre-select optimal area for placement of a left ventricular lead.

One exemplary embodiment uses the ventricular activation sequence as mapped from surface electrodes to pre-select an optimal location of a left ventricular lead in conjunction with other methods (e.g., motion maps) of looking at mechanical motion of the left ventricle. Activation data from external electrode leads may be mapped to certain gross regions of the left ventricle. For example, activation from left anterior electrodes may be mapped to the anterior left ventricle, activation from left-lateral electrodes may be mapped to the lateral wall of the ventricle, activation from posterolateral electrodes may be mapped to a posterolateral location of the left ventricle, and activation from left posterior electrodes may be mapped to a posterior location of the left ventricle.

A preliminary target location may be selected based on the latest area of contraction from the motion map, and electrical activation times from the external electrodes corresponding to that particular area may be chosen. The activation time-data from electrodes corresponding to a particular anatomic area may be averaged to represent the activation time over that particular region. If the activation data indicates early activation, e.g., if the activation time is less than a certain value (e.g., a value which can be about 80 milliseconds to about 100 milliseconds) as measured from onset of depolarization or if the activation time is less than a certain percentile of the latest activation recorded from the external electrodes (e.g., where this percentile can be any value from about 50% to about 75%), then that location may be ruled out as an optimal site (e.g., because of early activation-times). If the external electrode activation data indicates late activation in that area (e.g., the data does not satisfy the criteria of early activation described above) and the external electrodes situated in the corresponding anatomic area do not show signs of a local scar (e.g., including fractionations (multiple deflections), small q-waves at the onset followed by r-waves, where q/r ratio is between 20-30%, or signs of ST segment elevation), the preliminary target location may be selected for implanting the implantable electrode and/or lead. The signs of scarring described here may be often clinically used for diagnosing myocardial infarction and may be inspected visually as well. The activation map from surface electrodes as well as the motion map over at least one cardiac cycle corresponding to the preliminary target area may be displayed.

One exemplary method may combine data from electromechanical mapping and a likelihood score for scar to select an optimal site for implantable electrode and/or lead placement. The data for combination may include timing of mechanical contraction of different regions of the target ventricle, e.g., left ventricle, as determined from a motion map, motion curves and features of the motion curves (e.g., peak-amplitudes of motion curves in the different regions of the target ventricle), electrical activation data in different regions of the left ventricle, and electrical signals, e.g., surface electrocardiogram signals, from surface electrodes in close proximity to different regions of the left ventricle. The exemplary method may combine all these different pieces of information to come up with a recommendation of an optimal target site.

For example, a subset of possible candidate regions may be identified based on certain thresholds of electrical activation times and mechanical contraction times. Regions that are activating electrically later than a certain percentage of the latest electrical activation time among all target regions and mechanically contracting later than a certain percentage of the latest mechanical contraction times amongst all target regions may be chosen as potential candidate sites for lead placement. The certain percentages may be between about 70% and about 100%. Next, for example, each region from this subset may be assigned a scar risk score of 0-2 based on the one or more criteria and processes. For example, initially, all regions may be assigned a scar risk score of 0 and the following criteria are evaluated: peak-to-peak amplitude of a motion curve corresponding to a region being less than a selected percentage (e.g., 0% to about 50% such as 10%) of max peak-to-peak amplitude among all target regions may add 1 to the scar risk score for that region. Electrical signals (e.g., surface electrocardiogram electrodes) at or in proximity to the region showing one or more signs of scarring that includes ST segment elevation, fractionations, low peak-to-peak amplitudes (e.g., <1 mV) may add 1 to the scar risk score for that region. Once evaluation for scar risk scores is completed, the candidate regions may be sorted in descending order of scar risk score. The region with the lowest scar risk score may be selected as the final site for the lead. If all sites are at the highest scar risk score (e.g., 2), then new candidate sites may be selected by lowering each of the thresholds by a selected amount (e.g., about 10% to about 20%). For example if initial selected percentages were 75% each, new, lowered percentages may be 65%. In one embodiment, instead of using percentile thresholds, absolute thresholds may be used for one or more of the variables of interest (e.g., electrical activation times greater than or equal to a selected value between about 50 milliseconds and about 150 milliseconds).

One exemplary method may include identifying a candidate site for left ventricular (LV) lead implant on a 3-D model of cardiac sinus (CS) venous anatomy, reconstructing body-surface markers and finding the marker in closest proximity of the candidate site, determining surface electrocardiogram (ECG) electrodes (e.g., unipolar electrodes) in closest proximity to the marker previously found, and display an estimate, or surrogate, of electrical activation time (e.g., q-LV time) on a display module (e.g. monitor/screen, etc.) integrated with the 3D model/motion map. Further, the local electrical activation time (e.g., the q-LV time) may be estimated from the estimated, or surrogate, activation time determined from the ECG signals from surface electrodes identified previously.

One exemplary method may include determining mechanical contraction times at target sites during baseline rhythm (e.g., from motion map data of the target veins), determine electrical activation times in target sites during baseline rhythm via surrogate electrical activation times (e.g., q-LV times) acquired from a surface electrocardiogram (ECG) belt, identifying candidate sites from among mapped sites which are within a threshold (e.g., 75%) of the latest mechanical contraction and within a given threshold (e.g.

75%) of the latest electrical activation time, evaluating scar risk score from motion/strain curves and surface ECG signals for each of the candidate sites, and/or identifying optimal sites as the candidate sites with the lowest scar risk score.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 4 is a diagram of exemplary surface locations of a patient mapped to implantation site regions of the patient's heart.

FIG. 8 is a block diagram of an exemplary method of assisting in noninvasive location selection for an implantable electrode.

DETAILED DESCRIPTION OF EXEMPLARY EMBODIMENTS

Figure 1:
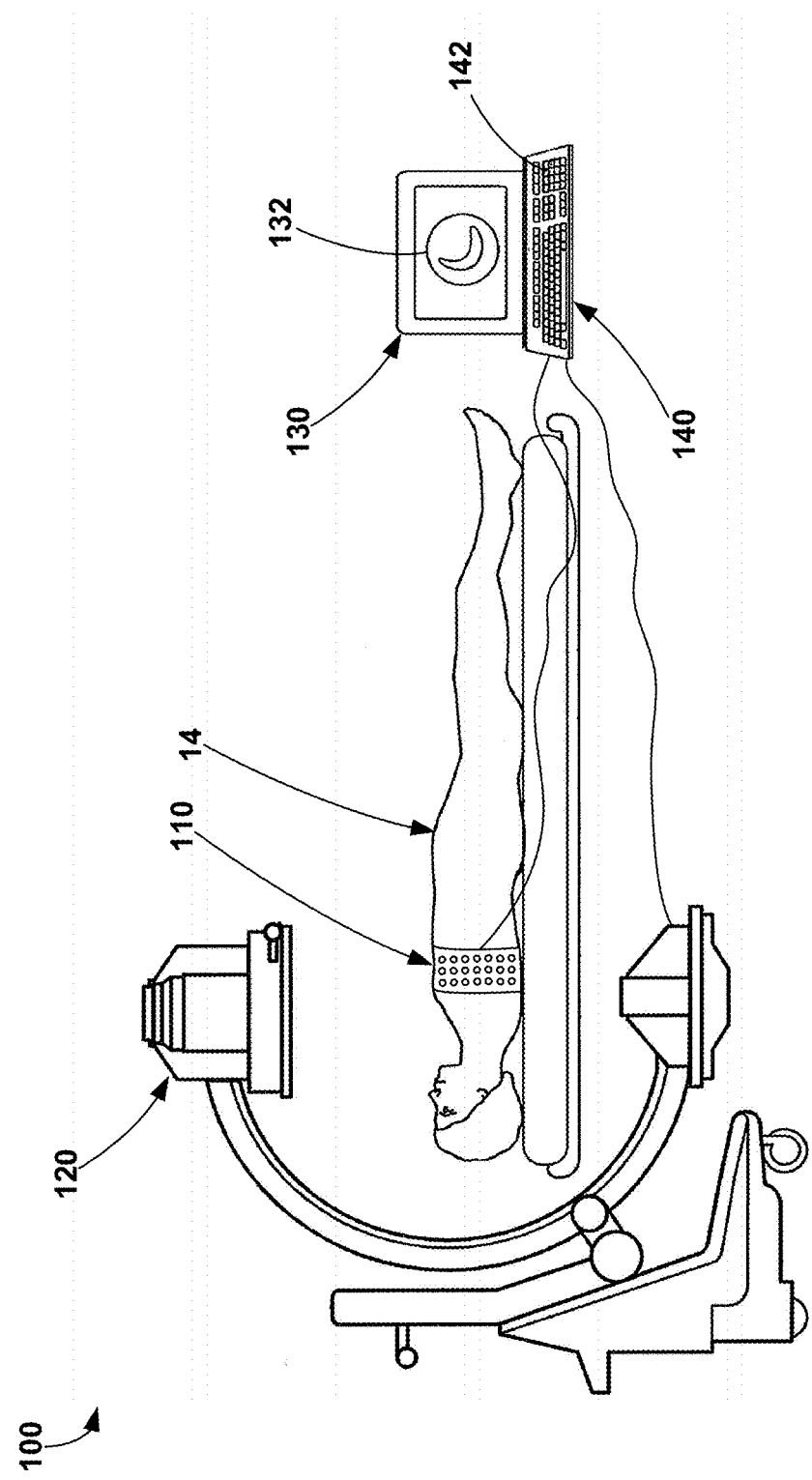
FIG. 1 is a diagram of an exemplary system including electrode apparatus, imaging apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, apparatus, and methods shall be described with reference to FIGS. 1-17. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

From unipolar electrocardiogram (ECG) recordings, electrical activation times can be detected or estimated in proximity of a reference location (e.g., which can be a chosen location for the left ventricle lead during implant). Such electrical activation times may be measured and displayed, or conveyed, to an implanter by a system which acquires the ECG signals and generates the metric of electrical activation (e.g., q-LV) time. As described herein, at least in one or more embodiments, electromechanical mapping to select a lead placement site for cardiac resynchronization therapy may use an algorithm that uses q-LV data (e.g., electrical activation times) in conjunction with mechanical motion map timings to best select a site for a LV lead. For example, such an algorithm may provide an optimizing scheme that takes into account electrical and mechanical times as well as any information about scar tissue that can be derived from ECG/motion profile/curve measurements.

As described herein, various exemplary systems, methods, and interfaces may be configured to use electrode apparatus including external electrodes, imaging apparatus, display apparatus, and computing apparatus to noninvasively assist a user (e.g., a physician) in selecting one or more locations (e.g., implantation site regions) proximate a patient's heart for one or more implantable electrodes and/or to navigate one or more implantable electrodes to the selected location(s). An exemplary system 100 including electrode apparatus 110, imaging apparatus 120, display apparatus 130, and computing apparatus 140 is depicted in FIG. 1.

The electrode apparatus 110 as shown includes a plurality of electrodes incorporated, or included within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis. Exemplary electrode apparatus 110 will be described in more detail in reference to FIGS. 3A-3B.

The imaging apparatus 120 may be any type of imaging apparatus configured to image, or provide images of, at least a portion of the patient in a non-invasive manner. For example, the imaging apparatus 120 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in selecting a location proximate a patient's heart for an implantable electrode, and after the exemplary systems, methods, and interfaces have provided noninvasive assistance, the exemplary systems, methods, and interfaces may then provide assistance to implant, or navigate, an implantable electrode into the patient, e.g., proximate the patient's heart.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 120 may be configured to capture, or take, x-ray images (e.g., two dimensional x-ray images, three dimensional x-ray images, etc.) of the patient 14. The imaging apparatus 120 may be operatively coupled (e.g., through one or wired electrical connections, wirelessly, etc.) to the computing apparatus 140 such that the images captured by the imaging apparatus 120 may be transmitted to the computing apparatus 140. Further, the computing apparatus 140 may be configured to control the imaging apparatus 120 to, e.g., configure the imaging apparatus 120 to capture images, change one or more settings of the imaging apparatus 120, etc.

It will be recognized that while the imaging apparatus 120 as shown in FIG. 1 may be configured to capture x-ray images, any other alternative imaging modality may also be used by the exemplary systems, methods, and interfaces described herein. For example, the imaging apparatus 120 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 120 may be configured to capture a plurality of consecutive images (e.g., continuously) to provide video frame data. In other words, a plurality of images taken over time using the imaging apparatus 120 may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 130 and the computing apparatus 140 may be configured to display and analyze data such as, e.g., surrogate electrical activation data, image data, mechanical motion data, etc. gathered, or collected, using the electrode apparatus 110 and the imaging apparatus 120 to noninvasively assist a user in location selection of an implantable electrode. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in location selection of an implantable electrode, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 to view and/or select one or more target or candidate locations of a portion of a patient's heart as further described herein.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including graphical depictions of anatomy of a patient's heart, images of a patient's heart, graphical depictions of locations of one or more electrodes, graphical depictions of one or more target or candidate locations, alphanumeric representations of one or more values, graphical depictions or actual images of implanted electrodes and/or leads, etc. For example, the display apparatus 130 may include a liquid crystal display, an organic light-emitting diode screen, a touchscreen, a cathode ray tube display, etc.

The graphical user interfaces 132 displayed by the display apparatus 130 may include, or display, one or more regions used to display graphical depictions, to display images, to allow selection of one or more regions or areas of such graphical depictions and images, etc. As used herein, a "region" of a graphical user interface 132 may be defined as a portion of the graphical user interface 132 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 132 may be defined as a portion of the graphical user interface 132 located with a region that is smaller than the region it is located within.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, image data from the imaging apparatus 120, electrical signal data from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.). The exact configuration of the computing apparatus 130 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

As used herein, mechanical motion data may be defined as data relating to the mechanical motion of one or more regions of a patient's heart such as portions of the walls of the patient's heart. It may be desirable for target locations in a patient's heart for implantable electrode placement to also have late mechanical motion timing (e.g., later motion than other portions of the patient's heart, motion that is later than a selected threshold value or time, etc.). Mechanical motion data may be measured and determined using the exemplary imaging apparatus 120 and the computing apparatus 140. For example, a plurality of frames of image data may be captured using the imaging apparatus 120 and analyzed by the computing apparatus to determine mechanical motion information, or data, of one or more regions of a patient's heart.

Local 3D motion of the heart wall can be decomposed into two components: the first component expresses change of distances between neighboring points and is referenced as a strain (e.g., contraction, when distances decrease or expansion, when distances increase, etc.) and the second non-strain component may not involve change of distances between neighboring points and may involve translation and/or rotation. The strain may be anisotropic. Specifically, a circumferential strain when cross sections (segments) perpendicular to the long axis of a heart chamber change length may be differentiated from a longitudinal strain when lines substantially parallel to long axis change length. The exemplary imaging apparatus 120 described herein may be configured to provide image data to provide graphical depictions of contraction and expansion as a change in scale of a blood vessel tree, or in other words, as a change of distance between points, while rotation and translation are visualized without change of distances.

The imaging apparatus 120, which may be a computerized X-ray machine, may be directed at the patient's heart and activated to produce a time sequence of X-ray images of the heart area at the field of view. In order to expose blood vessels (e.g., such as the coronary vessels) at the heart area under view, the X-ray images may be preferably obtained under angiography procedure by injecting contrast agent to the patient. Where the vessels to be detected are the coronary veins, the angiography may be carried out after a balloon is inserted and inflated inside the vein, e.g., the coronary sinus, so as to prevent blood flow from dispersing the contrast agent before the images are taken.

For example, a time sequence of two-dimensional X-ray projection images may be captured by imaging apparatus of FIG. 1 and stored by the computing apparatus 140. The two-dimensional images may be angiograms taken after the patient has been injected with contrast agent. The time sequence may include "snapshots" (e.g., angiographic cine-runs) of the coronary vessel under the same projection angle during at least part of the cardiac cycle of the patient. Further, the projection direction may be selected to be substantially orthogonal to the surface of the heart at the region of interest or to the main velocity component thereof.

The blood vessels of interest may be tracked through the time sequence of images in order to identify the movements of the vessels through at least part of the cardiac cycle. Tracking of blood vessels through the time sequence of images may be performed by calculation of local area transformations from one frame to the next, or by tracking selected control points in the detected vessels. Yet, in accordance with some embodiments, tracking the vessels may be performed by a hybrid combination of the two methods.

Examples of systems and/or imaging apparatus configured to capture and determine mechanical motion information may be described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which are incorporated herein by reference in their entireties.

Figure 2:
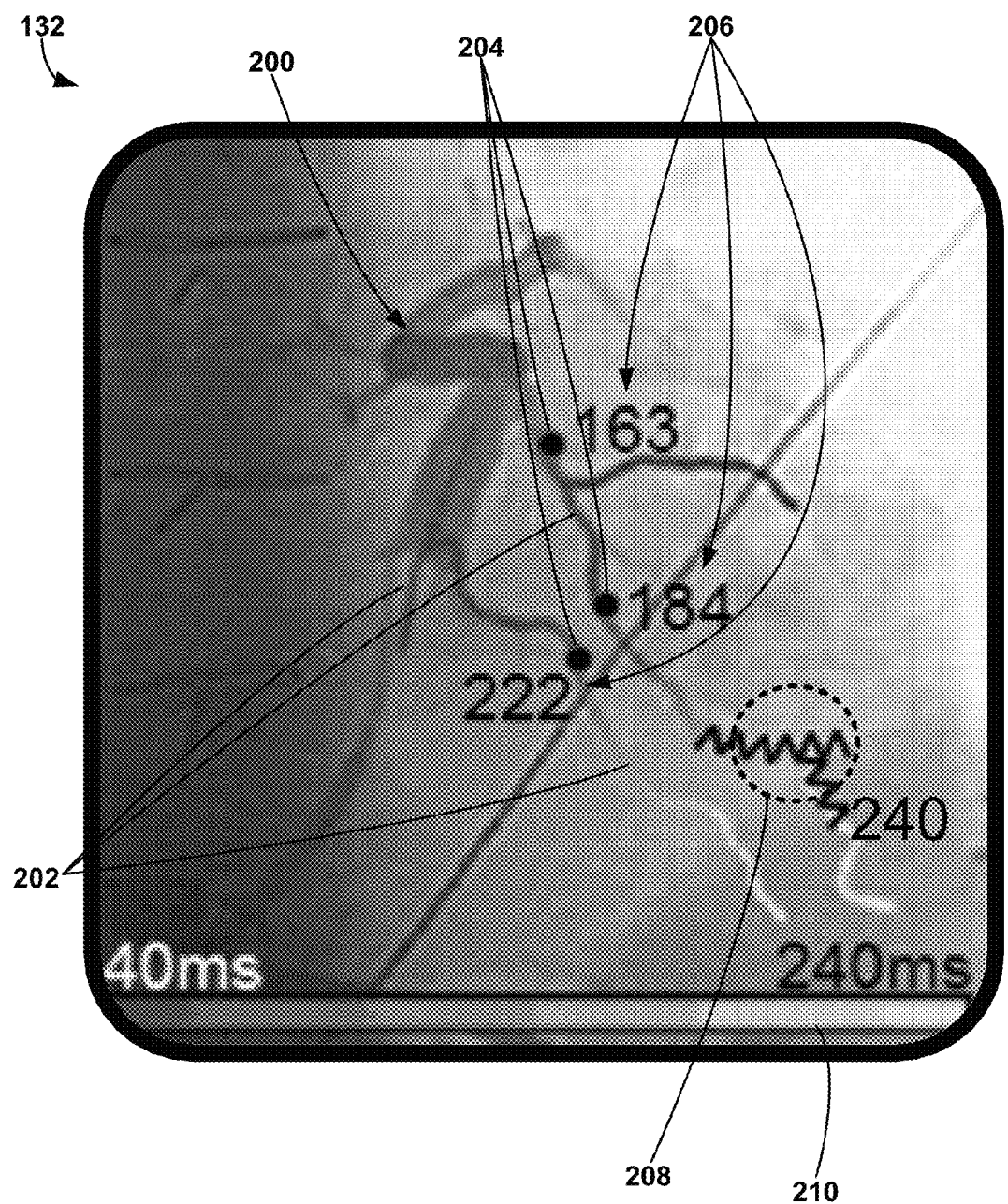
FIG. 2 is an exemplary graphical user interface depicting mechanical motion information of a portion of a patient's heart.

Mechanical motion data, or information, may be provided to a user to assist the user in selecting a location for an implantable electrode. An exemplary graphical user interface 132 depicting mechanical motion information of a portion of a patient's heart is shown in FIG. 2. The graphical user interface 132 is configured to depict at least a portion of blood vessel anatomy 200 of a patient's heart and mechanical motion information with respect to the blood vessel anatomy 200. As shown, the blood vessel anatomy 200 is the coronary sinus located proximate the left ventricle of a patient. The blood vessel anatomy 200 further includes a plurality of branches 202 of, e.g., the coronary sinus. Each branch, as well as multiple locations within each branch, may provide candidate site regions or locations for implantable electrodes. Implantable electrodes may be implanted in locations having the latest mechanical motion time. As used herein, mechanical motion time may be the time between the onset of contraction and a common fiducial point such as e.g., onset of QRS depolarization complex for that particular cardiac cycle on an external ECG lead.

As shown, the mechanical motion time may be represented by color/grey scaling, or coding, the blood vessel anatomy 200 according to a scale 210. As shown, the scale 210 extends from dark grey/colors, which correspond to about 40 milliseconds (ms), to light white/colors, which correspond to about 240 ms. As such, a user may view the graphical user interface 132 to see, or ascertain, the mechanical motions times of the different regions of the heart (e.g., different regions of the blood vessel anatomy). Additionally, the graphical user interface 132 may alphanumerically depict the mechanical motion times 206 for one or more regions 204 identified on blood vessel anatomy 200. Using the graphical user interface 132, a user may select a target, or candidate, location 208 for implantation that may have the latest, or near the latest, mechanical motion time. As shown, the target location 208 may have a mechanical motion time of 240 ms.

It may be desirable for target or candidate site regions or locations for implantable electrode placement to also have late electrical activation times, in addition to late mechanical motion times. The selected region, or location, such as region 208, however, may not have a late electrical activation time (e.g., indicating that the site may not be as desirable even though the mechanical motion time indicated its desirability as an implant site). As such, it is beneficial to have information about electrical activation times and mechanical motion times associated with a target or candidate site region to determine its suitability for implant.

Figure 3A:
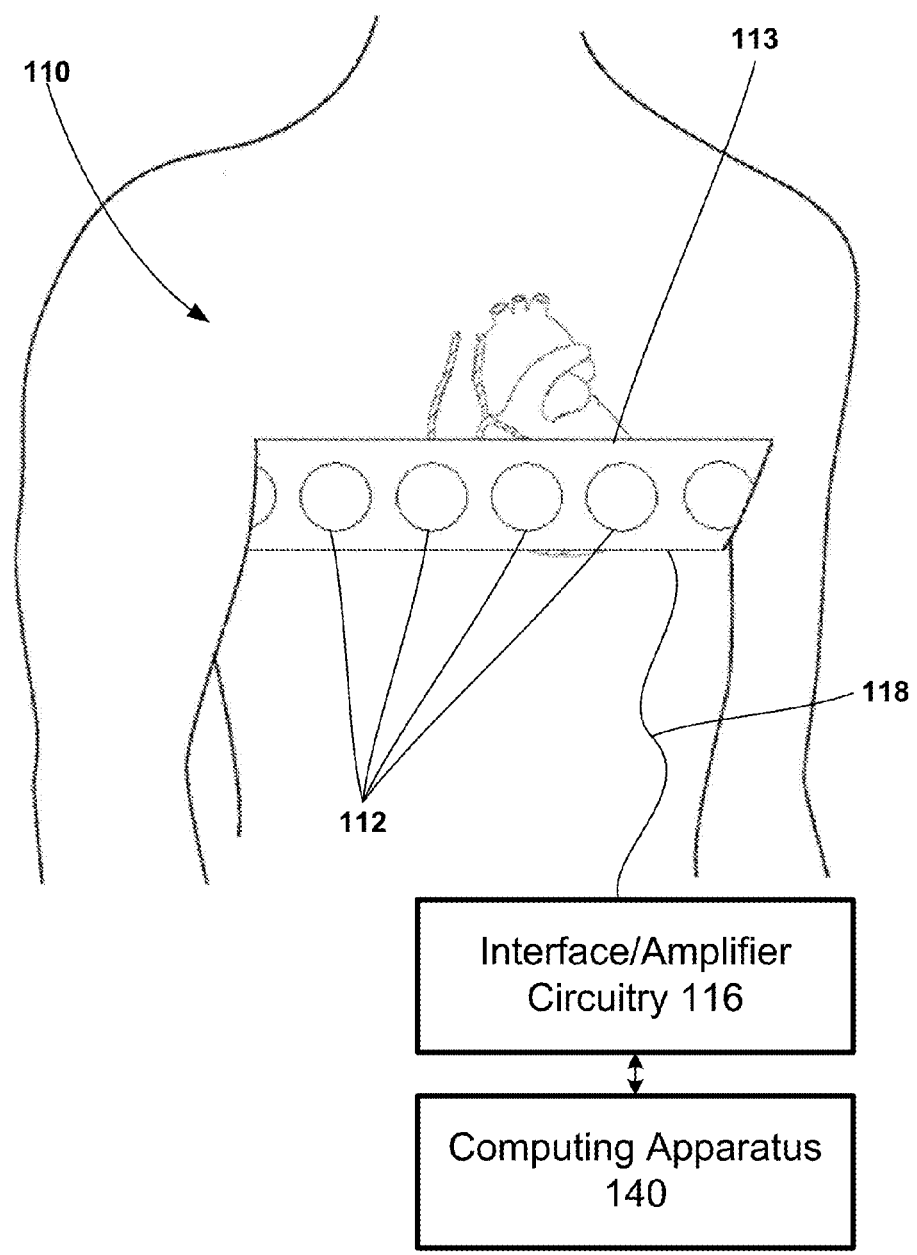
FIGS. 3A-3B are diagrams of exemplary external electrode apparatus for measuring torso-surface potentials.
Figure 3B:
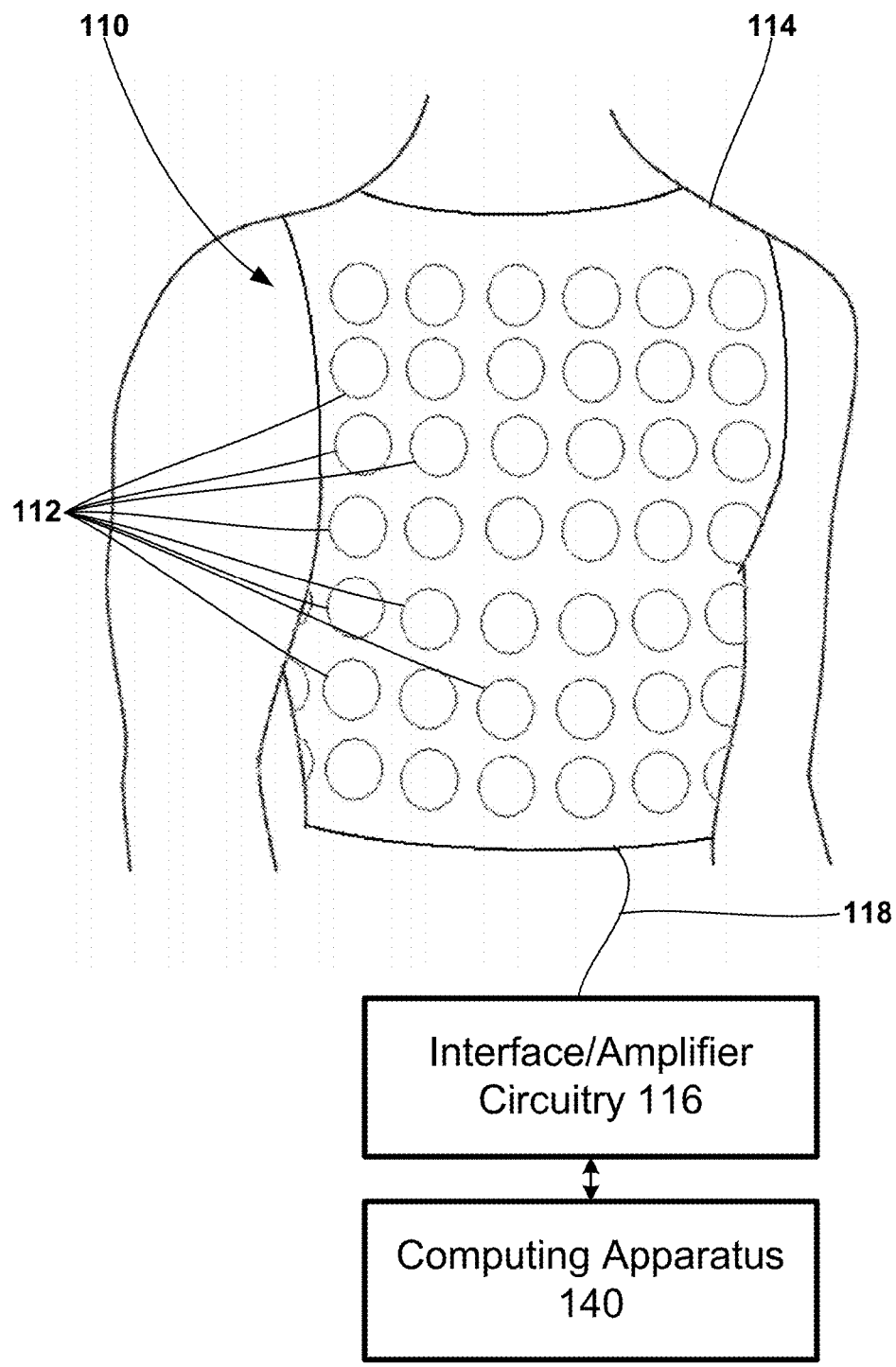

Electrical activation data of one or more regions of a patient's heart may be determined using electrode apparatus 110 as shown in FIG. 1 and in FIGS. 3A-3B. The exemplary electrode apparatus 110 may be configured to measure body-surface potentials of a patient 14 and, more particularly, torso-surface potentials of a patient 14. As shown in FIG. 3A, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of patient 14 such that the electrodes 112 surround the patient's heart. As further illustrated, the electrodes 112 may be positioned around the circumference of a patient 14, including the posterior, lateral, posterolateral, and anterior locations of the torso of patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data.

Although in the example of FIG. 3A the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other means of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide surrogate electrical activation data such as surrogate electrical activation times, e.g., representative of actual, or local, electrical activation times of one or more regions of the patient's heart as will be further described herein. Measurement of activation times can be performed by picking an appropriate fiducial point (e.g., peak values, minimum values, minimum slopes, maximum slopes, zero crossings, threshold crossings, etc. of a near or far-field EGM) and measuring time between the onset of cardiac depolarization (e.g., onset of QRS complexes) and the appropriate fiducial point (e.g., within the electrical activity). The activation time between the onset of the QRS complex (or the peak Q wave) to the fiducial point may be referred to as q-LV time.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to identify, select, and/or determine whether one or more regions of a patient's heart may be optimal, or desirable, for implantable electrode placement.

FIG. 3B illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 3A, the electrode apparatus 110 of FIG. 3B may include interface/amplifier circuitry 116 electrically coupled to each of the electrodes 112 through a wired connection 118 and configured to transmit signals from the electrodes 112 to computing apparatus 140. As illustrated, the electrodes 112 may be distributed over the torso of patient 14, including, for example, the anterior, lateral, and posterior surfaces of the torso of patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

As described herein, the electrode apparatus 110 may be configured to measure electrical information (e.g., electrical signals) representing different regions of a patient's heart. More specifically, activation times of different regions of a patient's heart can be approximated from surface electrocardiogram (ECG) activation times measured using surface electrodes in proximity to surface areas corresponding to the different regions of the patient's heart.

A diagram of exemplary surface locations of patient 14 mapped to regions of a patient's heart 12 to be measured using external electrode apparatus are shown in FIG. 4. As shown, a left anterior surface location 220 may correspond to a left anterior left ventricle region 230 of the patient's heart 12, a left lateral surface location 222 may correspond to a left lateral left ventricle region 232 of the patient's heart 12, a left posterolateral surface location 224 may correspond to a posterolateral left ventricle region 234 of the patient's heart 12, and a posterior surface location 226 may correspond to a posterior left ventricle region 236 of the patient's heart 12. Thus, the electrical signals measured at the left anterior surface location 220 may be representative, or surrogates, of electrical signals of the left anterior left ventricle region 230, electrical signals measured at the left lateral surface location 222 may be representative, or surrogates, of electrical signals of the left lateral left ventricle region 232, electrical signals measured at the left posterolateral surface location 224 may be representative, or surrogates, of electrical signals of the posterolateral left ventricle region 234, and electrical signals measured at the posterior surface location 226 may be representative, or surrogates, of electrical signals of the posterior left ventricle region 236.

Unipolar ECG data collected from electrode apparatus 110 such as, e.g., depicted in FIGS. 3A-3B, may be used to derive a sequence of ventricular activation. Information on regional, or local, ventricular activation may be inferred by looking at activation times corresponding to certain anatomic regions.

Figure 5:
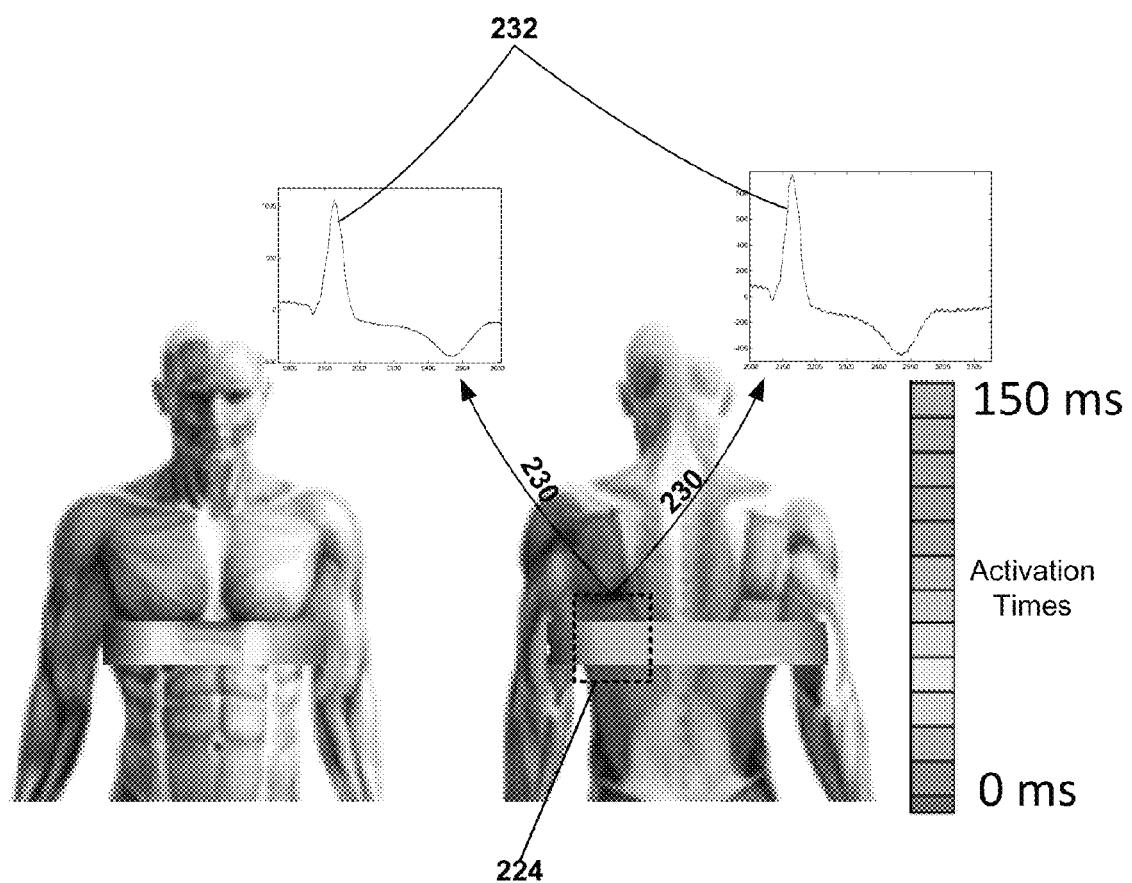
FIG. 5 is a diagram depicting late surrogate activation time in the posterolateral surface location of a patient measured using external electrodes.

A diagram depicting late surrogate activation time of a posterolateral surface location of a patient measured using external electrodes is depicted in FIG. 5. As shown, ECG activation data shows late activation (e.g., about 150 ms) in the posterolateral surface location 224, and thus the posterolateral left ventricle region 234, which corresponds to the posterolateral surface location area 224, may be a target, or candidate, implantation site region for an implanted electrode. Further, samples 230 from the posterolateral surface location 224 show broad, tall, and dominant R-waves 232 that may further indicate that the posterolateral left ventricle region 234 may be an optimal candidate, or target, implantation site region for an implanted electrode.

So that the computing apparatus 140 is aware of where the electrical signals measured using the external electrodes 112 of the electrode apparatus 110 are coming from (e.g., such as the various surfaces locations, or areas, for example, the left anterior surface location 220, the left lateral surface location 222, the left posterolateral surface location 224, the posterior surface location 226 etc.), the external electrodes 112 may be associated with one or more of the surface locations, or areas, and thus with one or more locations, or regions, of the patient's heart 14. Any suitable technique for associating the external electrodes (e.g., signals therefrom)

with one or more locations, or regions, of the patient's heart 14 may be used. For example, in one or more embodiments, to associate the external electrodes 112 with one or more surface locations and/or regions of the patient's heart, a user may particularly place, or locate, certain electrodes on particular locations of the patient's torso (e.g., one or more electrodes being in proximity to the region of the blood vessel anatomy for which measurements are to be provided). For example, one or more electrodes may be configured to measure, or be associated with, the left lateral surface location 222, and thus, a user may place such one or more electrodes on the left lateral surface location 232 (e.g., the one or more electrodes may be located proximate the left lateral surface location 232). In at least one embodiment, a band or vest may already have the electrodes 112 located in proper positions to correspond to various surface locations of a patient, and thus, a user may simply position the band or vest about the patient to properly locate the external electrodes 112 about the patient. The band or vest may further include indications of where each portion of the band or vest should be located about the patient.

Further, the external electrodes 112 may be associated with, or linked to, one or more surface locations and/or regions of the patient's heart using the imaging apparatus 120 described herein. For example, the electrodes 112 and/or markers (e.g., washers) may be visible in one or more images captured by the image apparatus 120. The markers may be located known distances and/or locations about the electrodes 112 such that markers may indicate where the electrodes 112 are located.

Using the imaging apparatus 120, which may image the electrodes 112 and/or markers with respect to at least a portion of the patient's heart 12, the electrodes 112 may be associated with the regions of the patient's heart 12 that the electrodes 112 are located in closest proximity to (e.g., about 0.5 centimeters to about 10 cm). For example, a first group of external electrodes 112 (e.g., a first group including one or more external electrodes) may be determined to be located in proximity to the left lateral left ventricular region 232 using images captured by the imaging apparatus 120, and thus, the first group of external electrodes 112 may be associated with the left lateral left ventricular region 232 of the patient's heart 12.

Figure 6:
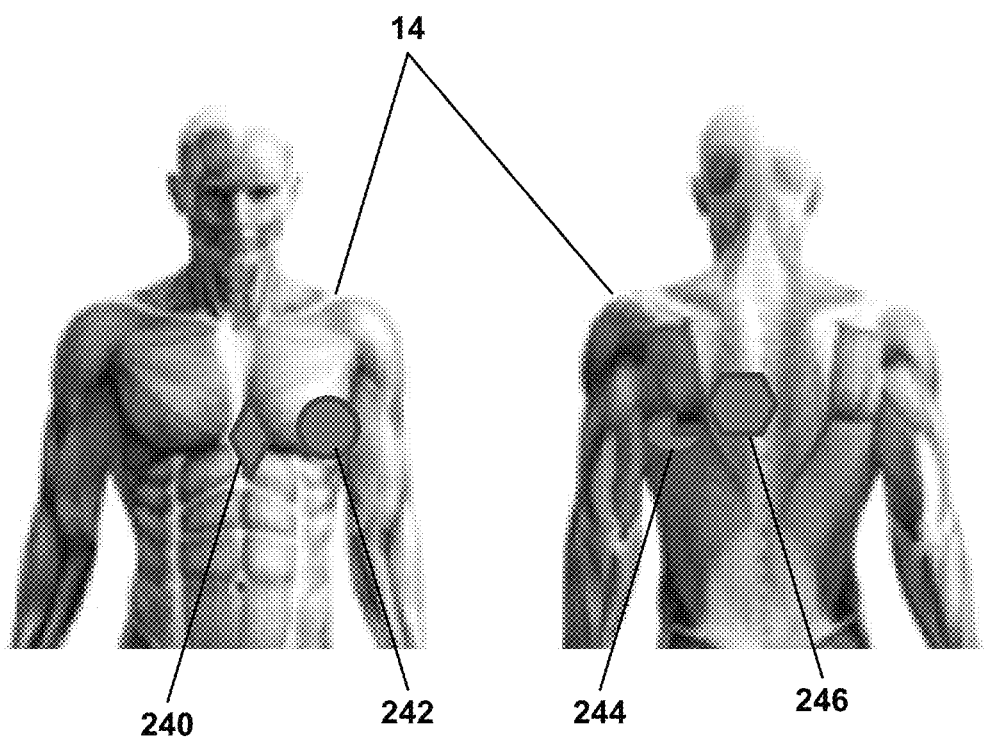
FIG. 6 is a diagram depicting locations of external markers associated with one or more external electrodes.

A diagram of surface locations of external markers associated with one or more electrodes used to measure surrogate electrical activation times is depicted in FIG. 6. As shown, a first marker 240, a second marker 242, a third marker 244, and a fourth marker 246 are depicted on patient 14. Each of the markers 240, 242, 244, 246 may be associated with one or more external electrodes 112. The imaging apparatus 120 may capture one or more images of a portion of the patient's heart and the markers 240, 242, 244, 246, and the computing apparatus 140 may determine which markers, and thus, which external electrodes, are proximate to the one or more different regions of the patient's heart.

Figure 7:
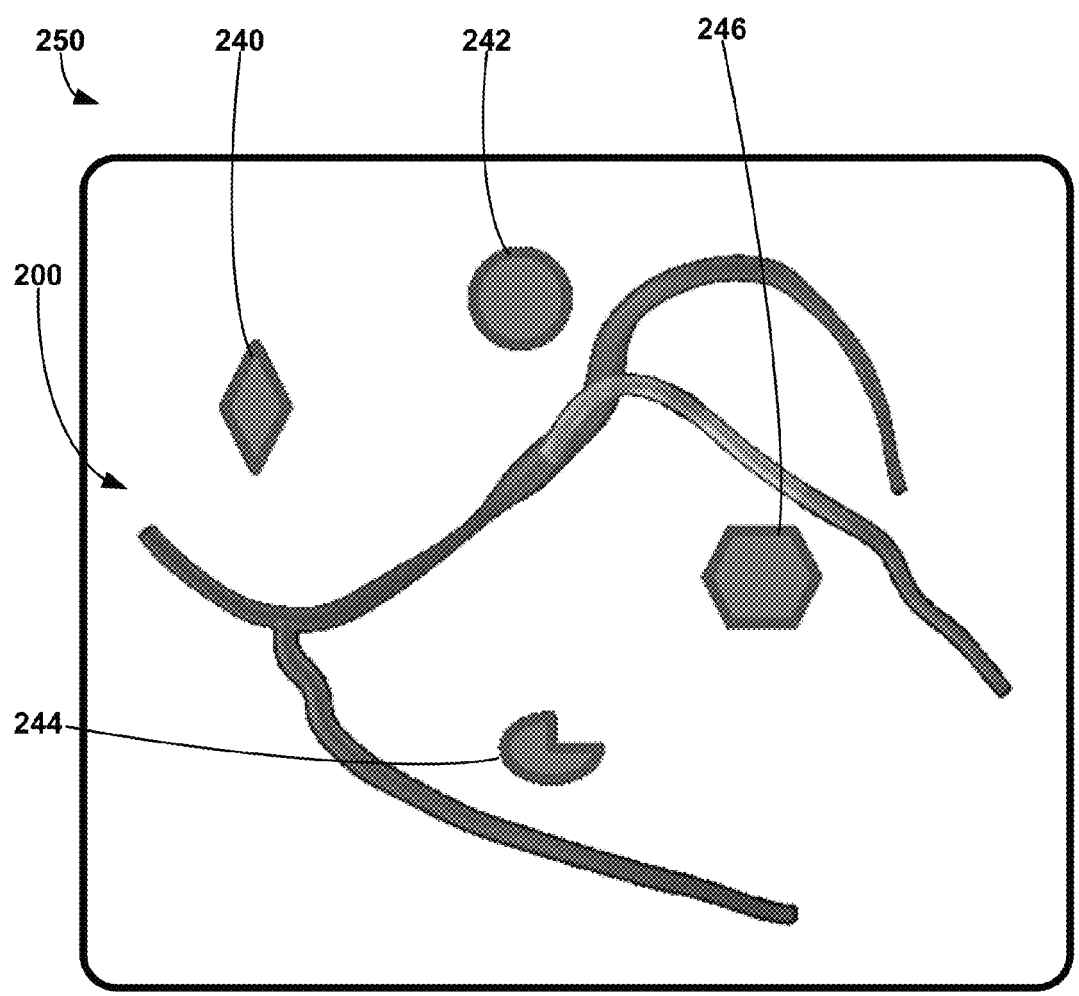
FIG. 7 is an exemplary graphical user interface depicting blood vessel anatomy, mechanical motion information thereof, and locations of the external markers of FIG. 6.

The locations of the markers may be further depicted on exemplary graphical user interfaces depicting a portion of the patient's heart. For example, an exemplary graphical user interface 250 depicting blood vessel anatomy 252 of a portion of a patient's heart, mechanical motion information associated with the blood vessel anatomy 252 (e.g., the mechanical motion information being color coded/grey scaled on the blood vessel anatomy), and the locations of the external markers 240, 242, 244, 246 with respect to the blood vessel anatomy 252 is shown in FIG. 7.

An exemplary method 260 of assisting in noninvasive location selection for an implantable electrode is depicted in FIG. 8. The exemplary method 260 may be described as being non-invasive because no lead, electrode, probe, or other device may be implanted into the patient when using the exemplary method. Further, the exemplary method 260 may be executed using the systems, apparatus, and graphical user interfaces described herein.

Figure 9A:
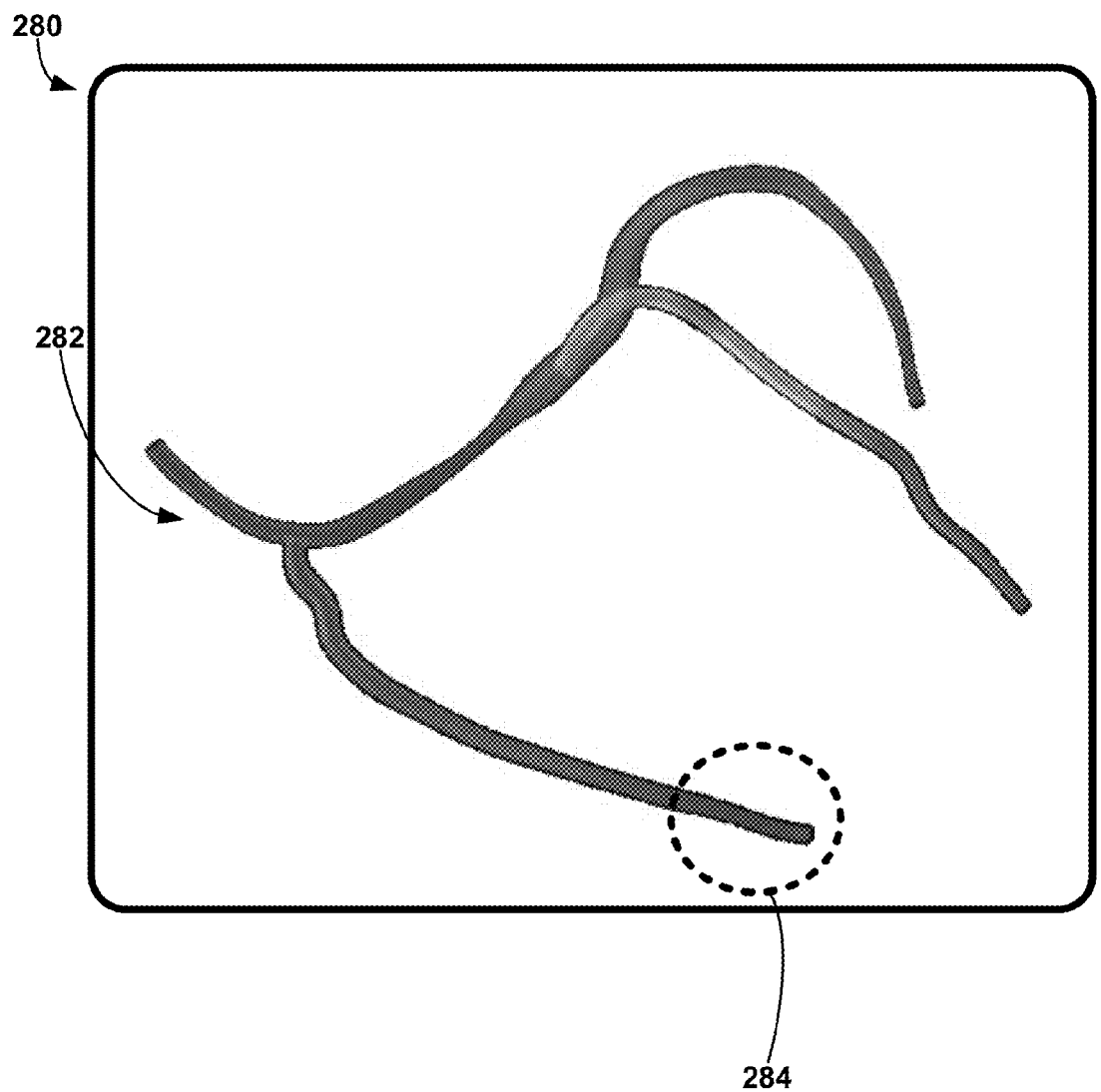
FIGS. 9A-9B are exemplary graphical user interfaces depicting blood vessel anatomy configured to allow a user to select an implantation site region of a patient's heart.

The exemplary method 260 may include displaying blood vessel anatomy 262 of at least a portion of a patient's heart, e.g., using a graphical user interface on display apparatus. Although the exemplary method 260 displays blood vessel anatomy of a patient's heart, it is to be understood that any part of a patient's anatomy may be displayed. The method 260 may further include measuring mechanical motion 264 of the blood vessel anatomy of the patient's heart and displaying mechanical motion information 266 of the blood vessel anatomy, e.g., using a graphical user interface on a display apparatus. An exemplary graphical user interface 280 including blood vessel anatomy 282 and gray-scaled mechanical motion information is shown in FIG. 9A. The blood vessel anatomy and mechanical motion information thereof may be captured using the imaging apparatus 120 described herein, which may be configured to image at least a portion of blood vessel anatomy of the patient's heart and provide image data used by the computing apparatus 140 to provide mechanical motion information or data.

A user may view and/or use the graphical user interface 280 of FIG. 9A to determine, or identify, one or more candidate site regions of the displayed portion of the patient's heart for implantation of implantable electrodes. For example, a user may view the mechanical motion information, e.g., grey-scaling or color-coding applied to the blood vessel anatomy in FIG. 9A, and identify a candidate site region 284 of the patient's heart based on the mechanical motion information. For example, a user may identify one or more regions having, e.g., mechanical motion times greater than a threshold, having the longest mechanical motion time, etc. A user may select the identified candidate region 284 using the graphical user interface 280 and input apparatus 142 of the computing apparatus 140. For example, if the input apparatus 142 is a touchscreen, the user may touch the identified candidate site region 284 with their finger or stylus. Further, for example, if the input apparatus 142 is a mouse, a user may "click on" the identified candidate site region 284 using the mouse.

Although a user is described as identifying the candidate region 284, the computing apparatus 140 and/or another portion of the system 100 may be configured to identify the candidate site region 284. For example, the computing apparatus 140 may be configured to automatically identify one or more regions of the blood vessel anatomy based on the mechanical motion information, e.g., implantation site region(s) having the longest mechanical motion time, implantation site region(s) have a mechanical motion time greater than or equal to a threshold value, etc.

The exemplary method 260 may further include measuring surrogate electrical activation time 270 of the identified candidate site region 284 using one or more external electrodes 112 located proximate tissue of a patient (e.g., skin of the patient's torso). As described herein the surrogate electrical activation time of a region, such as the candidate site region 284, may be measured using one or more external electrodes proximate the implantation site region.

In at least one embodiment, the positions of the external electrodes may be identified with respect to the implantation site region of the blood vessel anatomy using imaging apparatus 120, and the one or more external electrodes that are closest to a particular implantation site region (e.g., determined to be closest) may be used to measure surrogate electrical activation time for the implantation site region. In at least one embodiment, each external electrode may already be associated with a particular implantation site region of the blood vessel anatomy, and thus, the external electrodes already associated with an implantation site region may be used to measured surrogate electrical activation time for the implantation site region.

Figure 9B:
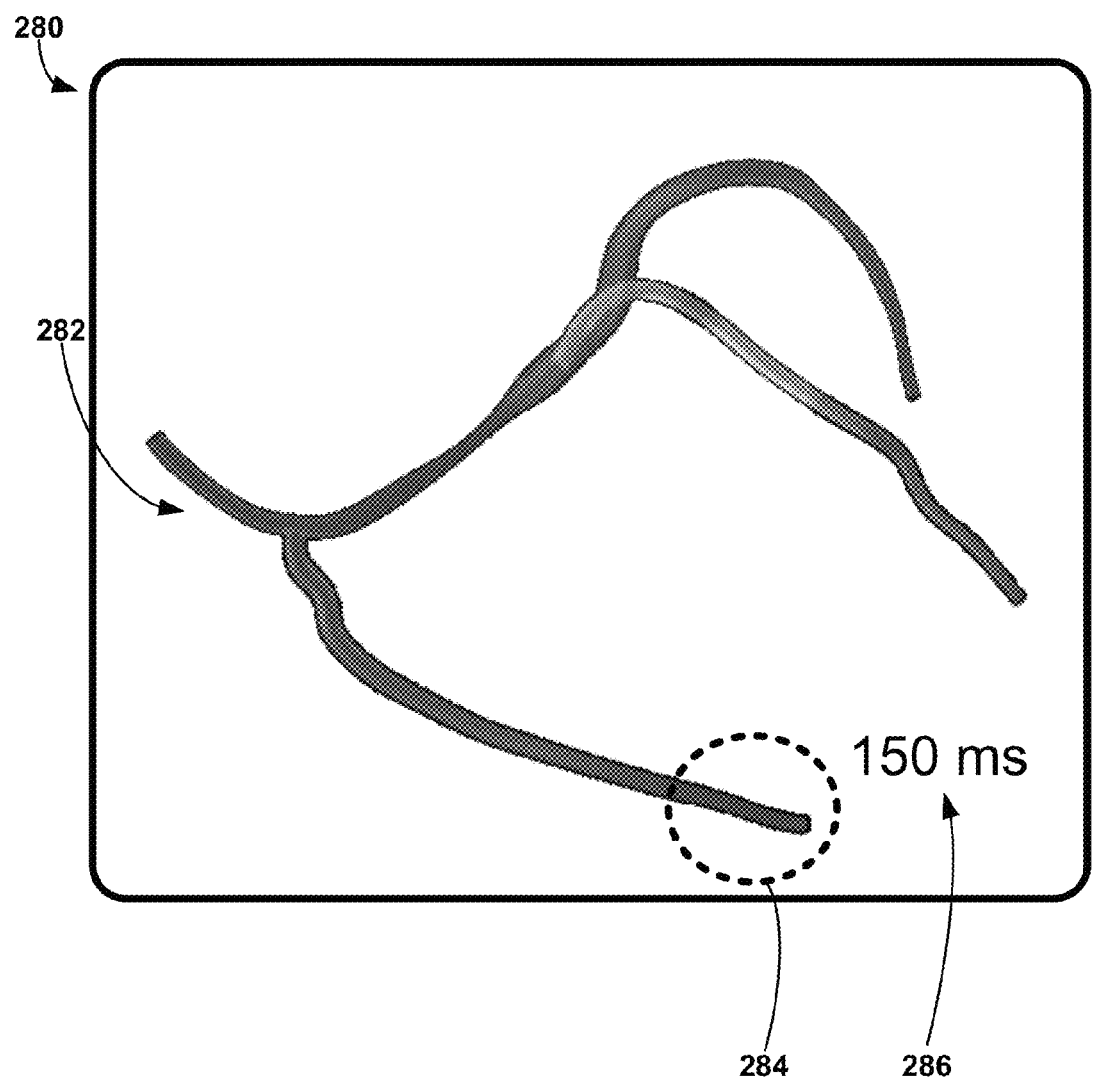

After the implantation site region of the blood vessel anatomy has been selected 268 and the surrogate electrical activation time has been measured 270, the exemplary method 260 may include displaying the measured surrogate activation time for the identified implantation site region 284. For example, the measured activation time 286 may be alphanumerically depicted proximate the identified implantation site region 284 of the blood vessel anatomy 282 on the graphical user interface 280 as shown in FIG. 9B. If the identified implantation site region does not have a desirable surrogate electrical activation time 286 (e.g., the implantation site region does not have a late electrical activation time, the electrical activation time is not greater than or equal to a threshold value, etc.), a user may select another implantation site region of the blood vessel anatomy 282, e.g., as shown by the arrow 271 looping back to identifying an implantation site region of blood vessel anatomy 268.

A user may then use the exemplary systems and interfaces described herein to navigate an implantable electrode to one or more of the identified implantation site regions 274. For example, the systems and graphical user interfaces described herein may provide real-time navigation of an implantable electrode (e.g., located on a lead, a wireless electrode, located on a device, etc.) to an implantation site region such as the identified implantation site region (e.g., a site region identified noninvasively as being associated with a late mechanical motion time and a late electrical activation time).

Figure 10:
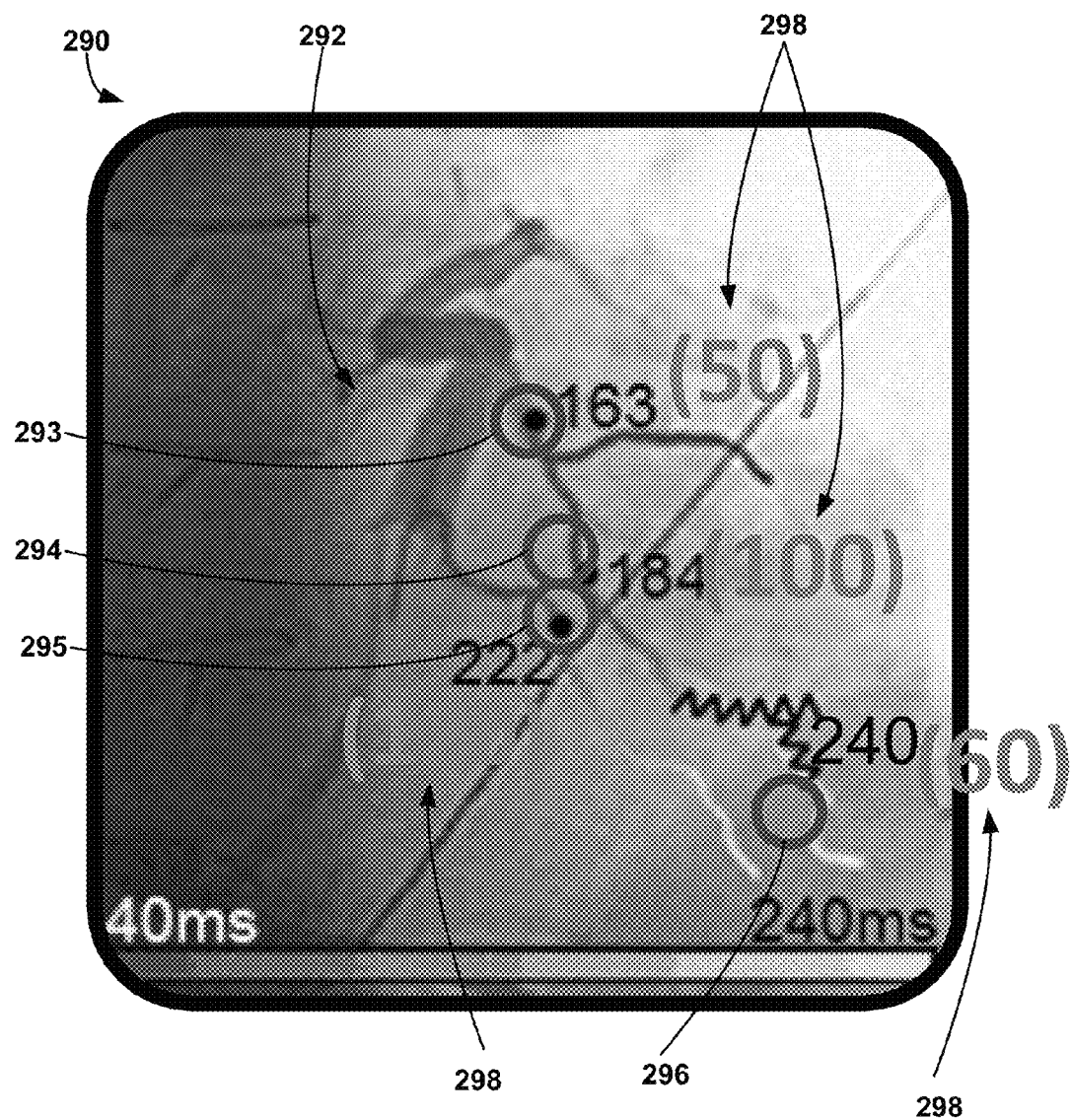
FIG. 10 is an exemplary graphical user interface depicting a region of a patient's heart including blood vessel anatomy, mechanical motion information and surrogate electrical activation information.

Although the exemplary method 270 may measure the surrogate electrical activation time 270 after an implantation site region of the blood vessel anatomy has been identified 268, it is to be understood that the exemplary systems, methods, and/or interfaces may be configured to measure surrogate electrical activation time 270 of a plurality of implantation site regions of the patient's heart prior to the identification of a particular region 268 and/or may display the measured surrogate electrical activation times 272 of all the implantation site regions. For example, an exemplary graphical user interface 290 depicting a portion of a patient's heart and blood vessel anatomy 292 thereof including mechanical motion information such as grey-scaling and alphanumeric values representing mechanical motion timings is shown in FIG. 10. The exemplary graphical user interface 290 further depicts surrogate activation times 296 for each of the first implantation site region 293, second implantation site region 294, third implantation site region 295, and fourth implantation site region 296.

Figure 11:
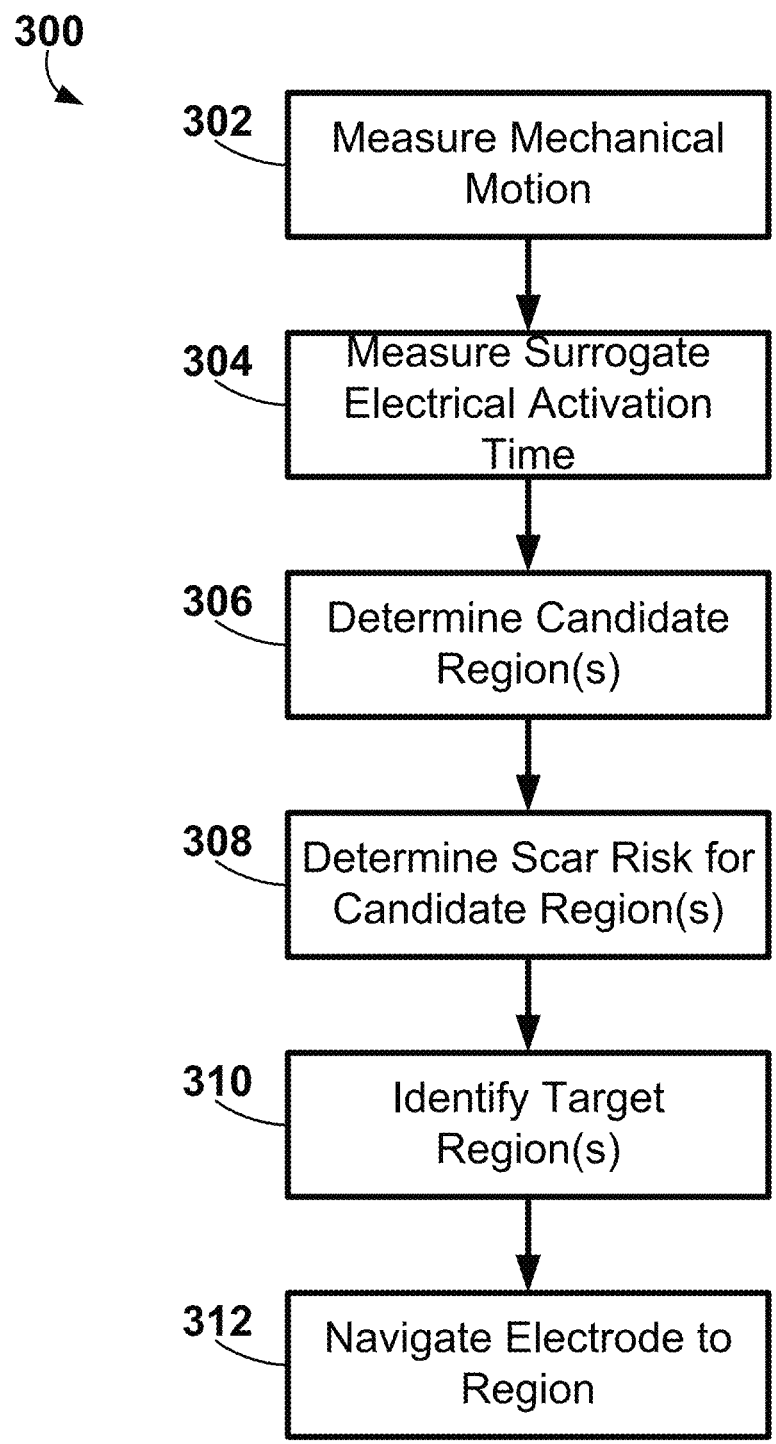
FIG. 11 is a block diagram of another exemplary method of assisting in noninvasive location selection for an implantable electrode.

One or more exemplary systems, methods, and/or interfaces may use measured mechanical motion data and measured surrogate electrical activation times to identify one or more candidate and/or target site regions for implantation, or location selection, of an implantable electrode for delivering therapy (e.g., from a larger number of potential implantation sites). An exemplary method 300 of assisting in such non-invasive location selection for an implantable electrode is depicted in FIG. 11. Generally, the exemplary method 300 may (e.g., automatically or by user selection) determine one or more candidate and/or target site regions for implanting an implantable electrode for delivery of therapy based on mechanical motion information of a portion of a patient's heart, surrogate electrical activation times of implantation site regions of the patient's heart, and, optionally, information relating to scar risk for one or more implantation site regions of the patient's heart.

The exemplary method 300 may include measuring mechanical motion 302 of a plurality of implantation site regions (e.g., identified site regions, such as, for example, the first implantation site region 293, the second implantation site region 294, the third implantation site region 295, and the fourth implantation site region 296 shown on the graphical user interface 290 of FIG. 10) of a portion of blood vessel anatomy of a patient's heart using, e.g., imaging apparatus 120, to provide mechanical motion data, or information, such as mechanical contraction times. Each implantation site region may be a defined portion or area of the patient's heart and/or of the blood vessel anatomy of the patient's heart. Further, each implantation site region may be different that the other implantation site regions. In other words, the implantation site regions may not be duplicative.

Surrogate electrical activation time may be measured 304 for each of the implantation site regions using, e.g., electrode apparatus 110, such that each implantation site region has a mechanical contraction time and surrogate electrical activation time associated therewith (e.g., measurements using one electrode of the electrode apparatus for each site region, averaged measurements from multiple electrodes of the electrode apparatus for each site region, etc.).

In one exemplary embodiment, the measured mechanical contraction times and measured surrogate electrical activation times for the first implantation site region 293, the second implantation site region 294, the third implantation site region 295, and the fourth implantation site region 296 of the portion of a patient's heart from the graphical user interface 290 of FIG. 10 is depicted below in Table 1.

TABLE 1

| Site # | Mechanical Times | Electrical Times |
|---|---|---|
| 1 | 163 ms | 50 ms |
| 2 | 184 ms | 100 ms |
| 3 | 222 ms | 120 ms |
| 4 | 240 ms | 60 ms |

The exemplary method 300 may then determine one or more candidate site regions 306 from the plurality of implantation site regions based on the measured mechanical contraction times and measured electrical activation times. The determination of one or more candidate site regions 306 may use comparisons, percentages, thresholds, averages, means, peak-to-peak amplitudes, maximum slope, minimum slope, other motion curve metrics, etc. of the measured mechanical contraction times and/or the measured surrogate electrical activation times.

For example, each of the mechanical contraction times may be compared to a threshold value or time to determine whether the implantation site region may be a candidate site region. The threshold value or time may be a fixed, or set, value determined, e.g., by a user or the computing apparatus, or may be based or calculated on other data such as some or all of the measured mechanical contraction times for the implantation site regions. For example, a mechanical motion threshold value or time may be based on the latest mechanical motion contraction time measured among the implantation site regions.

In the example depicted in FIG. 10 and Table 1, the fourth implantation site region 296 has the latest mechanical contraction time, which is 240 ms. The mechanical motion threshold value may be a selected percentage, such as, e.g., 50%, 60%, 65%, 70%, 75%, 80%, 90%, 95%, etc., of the latest mechanical contraction time. In this example, the selected percentage may be 75%, which would yield a mechanical motion threshold of 180 ms (e.g., 240 ms×75%=180 ms).

Each of the surrogate electrical activation times may be compared to a threshold value or time to determine whether the implantation site region may be a candidate site region. The threshold value or time may be a fixed, or set, value determined, e.g., by a user or the computing apparatus, or may be based or calculated on other data such as some or all of the measured surrogate electrical activation times for the implantation site regions. For example, an electrical activation threshold value or time may be based on the latest surrogate electrical activation time measured among the implantation site regions.

In the example depicted in FIG. 10 and Table 1, the third implantation site region 295 has the latest surrogate electrical activation time, which is 120 ms. The electrical activation threshold value may be a selected percentage, such as, e.g., 50%, 60%, 65%, 70%, 75%, 80%, 90%, 95%, etc., of the latest surrogate electrical activation time. In this example, the selected percentage may be 75%, which would yield an electrical activation threshold of 90 ms (e.g., 120 ms×75%=90 ms).

Using the mechanical motion threshold value and the electrical activation threshold value, the exemplary method 300 may determine one or more candidate site regions 306. For example, an implantation site region may be identified or selected as a candidate site region if the implantation site region has a mechanical contraction time greater than or equal to the mechanical motion threshold and a surrogate electrical activation time greater than or equal to the electrical activation threshold. As such, in the example of FIG. 10 and Table 1, the candidate sites must have a mechanical contraction time greater than or equal to 180 ms, i.e., the mechanical motion threshold value, and a surrogate electrical activation time greater than or equal to 90 ms, i.e., the electrical activation threshold value. Using such thresholds, the exemplary method 300 may determine that the second site 294 and third site 295 may be candidate site regions 306 for implantation of an implantable electrode to deliver therapy.

Additionally, if none of the implantation site region satisfies both the electrical activation threshold value and the mechanical motion threshold value, the threshold values may be decreased by a selected value or percentage, and each of the implantation site regions may be re-evaluated. In at least one embodiment, the selected percentages used to calculate the threshold values may be decreased by a fixed amount such as, e.g., 5%. Likewise, if all the implantation site regions satisfy both the electrical activation threshold value and the mechanical motion threshold value, the threshold values may be increased by a selected value or percentage, and each of the implantation site regions may be re-evaluated. Further, if only one implantation site region satisfies the electrical activation threshold value and the mechanical motion threshold value, this site region may be selected for implantation of the electrode.

The exemplary method 300 may also include graphically identifying the one or more candidate site regions 310 for implantation of the implantable electrode, e.g., using the exemplary graphical user interfaces described herein, etc. For example, the candidate site regions may be highlighted on a graphical user interface, or arrows may be depicted pointing to the candidate site regions selected from the originally or initially identified potential site regions.

Each of the one or more candidate site regions may have an associated scar risk. As such, the exemplary systems, methods, and graphical user interfaces may optionally consider the scar risk for each of the one or more candidate site regions to further selected one or more target site regions from the candidate site regions (e.g., reducing the number of site regions that may be desirable for electrode implantation). For example, the exemplary method 300 may include determining a scar risk for each of the candidate site regions 308, and based on the scar risk, identify the target site regions from the candidate site regions 310. Similar to the exemplary method 260, the exemplary method 300 may include navigating an implantable electrode to one or more of the candidate and/or target site regions 312 (e.g., after the candidate or target site region has been selected noninvasively). For example, the systems and graphical user interfaces described herein may provide real-time navigation of an implantable electrode (e.g., located on a lead, a wireless electrode, located on a device, etc.) to an implantation site region (e.g., a site region identified noninvasively using both mechanical motion times and electrical activation times, as well as optionally scar risk information).

Figure 12:
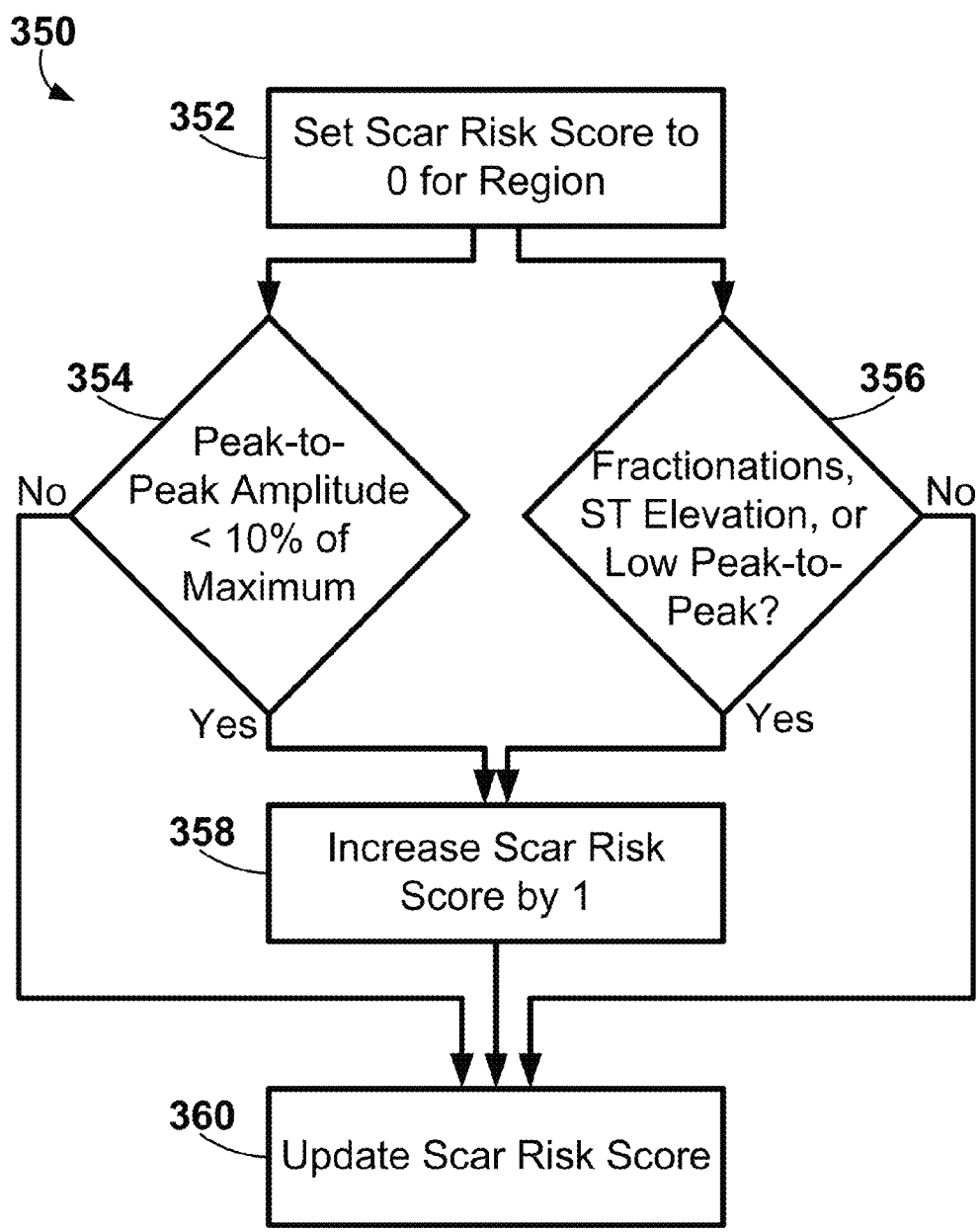
FIG. 12 is a block diagram of an exemplary method of noninvasively determining scar risk for an implantable site region of a patient's heart.
Figure 13:
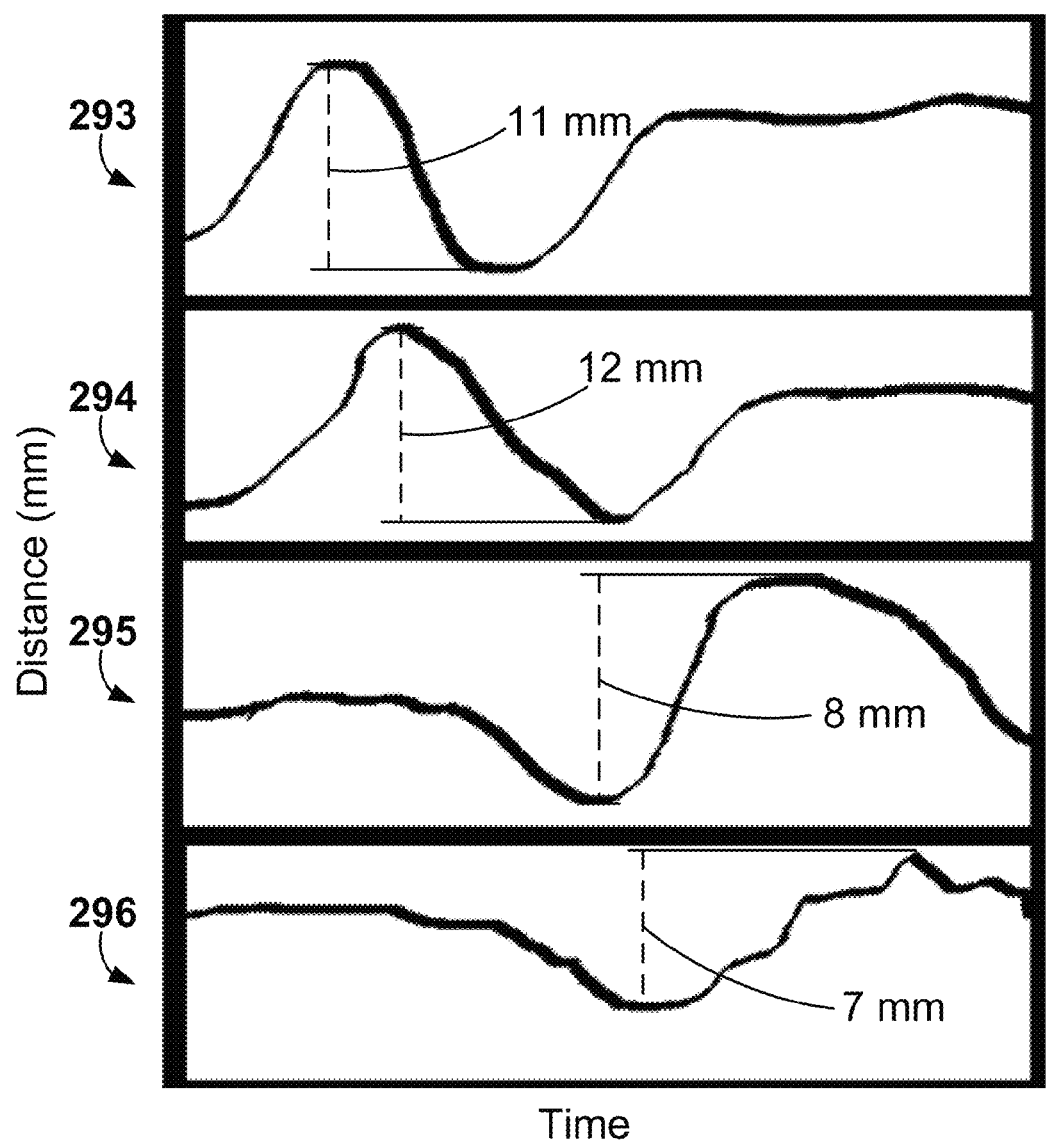
FIG. 13 shows graphs of mechanical motion information for four different implantable site regions of a patient's heart.
Figure 14:
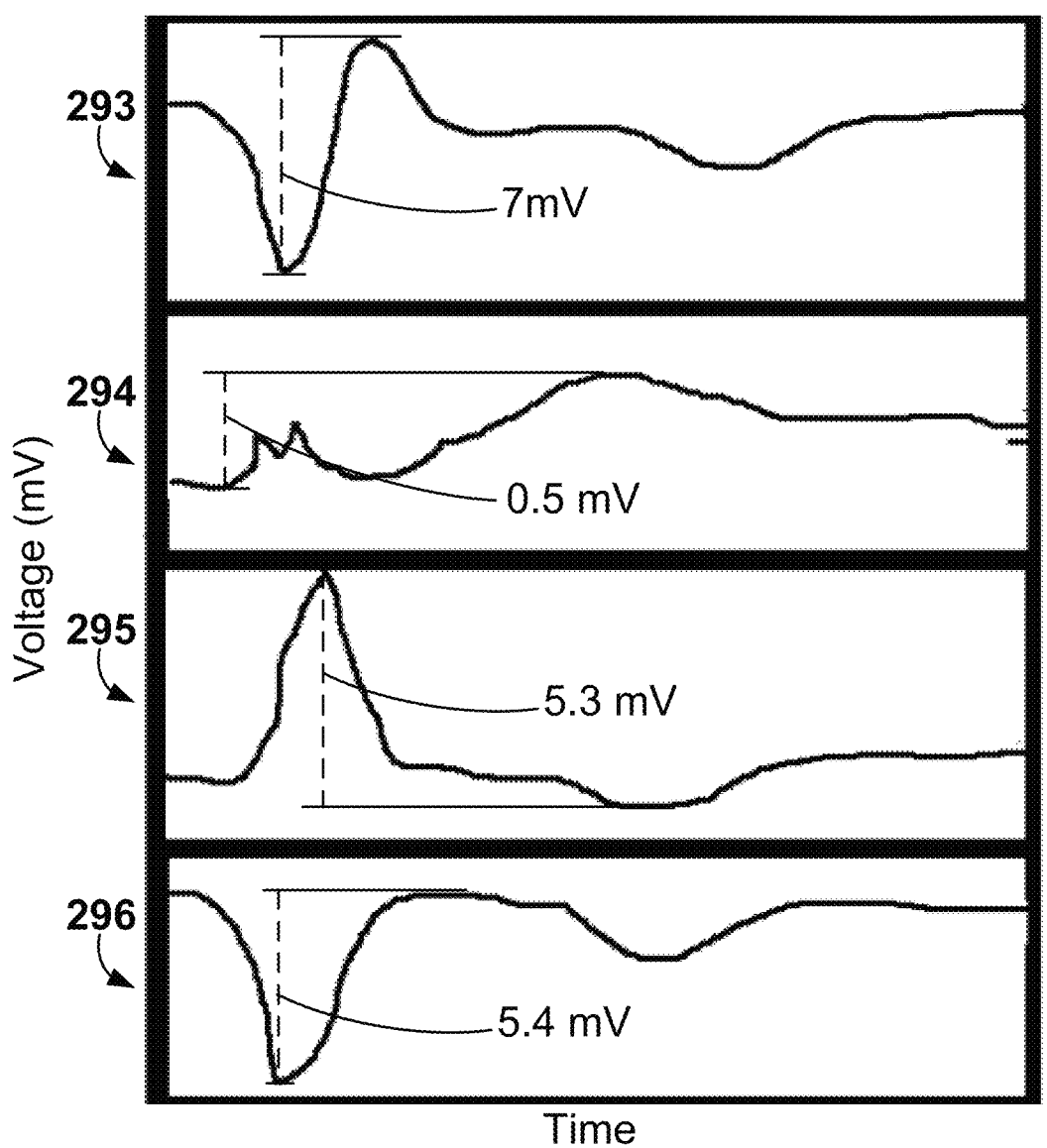
FIG. 14 shows graphs of surrogate electrical information for the four different implantable site regions of the patient's heart of FIG. 13.

As described herein, scar risk information may be used to further reduce the number candidate sites suitable for electrode implant. Although, any process of reducing the number of candidate sites based on scar information may be used, one exemplary method 350 of using scar risk information for noninvasively selecting implantation site regions is depicted in FIGS. 12-14. The exemplary method 350 may first set the scar risk score for a particular region (e.g., selected from the one or more candidate regions, etc.) to zero. The mechanical motion data and/or surrogate electrical data for that particular region may be evaluated to determine the scar risk score. For example, the mechanical motion data, or curve, may be evaluated as described with reference to FIG. 13, and the surrogate electrical activation data, or curve, may be evaluated as described with reference to FIG. 14.

The mechanical motion data, or curves, for the first implantation site region 293, the second implantation site region 294, the third implantation site region 295, and the fourth implantation site region 296 during one cardiac cycle are depicted in FIG. 13. As shown, the maximum peak-to-peak values for the first implantation site region 293, the second implantation site region 294, the third implantation site region 295, and the fourth implantation site region 296 are 11 millimeters (mm), 12 mm, 8 mm, and 7 mm, respectively.

A threshold value may be determined based on the maximum peak-to-peak amplitude. In this example, the maximum peak-to-peak amplitude of the implantation site regions may be 12 mm. For example, a threshold for indication of scarring may be 10% of the maximum peak-to-peak amplitude, and therefore, the threshold may be 1.2 mm.

The exemplary method 300 may increase the scar risk score for a particular implantation site region by one 358 if the implantation site region's peak-to-peak amplitude is less than the threshold value 354 (which, e.g., is 10% of the maximum peak-to-peak amplitude of all the implantation site regions). In the example depicted in FIG. 13, none of the first implantation site region 293, the second implantation site region 294, the third implantation site region 295, and the fourth implantation site region 296 have a peak-to-peak amplitude less than 1.2 mm, and thus, the scar risk score for each of the first implantation site region 293, the second implantation site region 294, the third implantation site region 295, and the fourth implantation site region 296 is not increased.

The surrogate electrical activation data, or curves, for the first implantation site region 293, the second implantation site region 294, the third implantation site region 295, and the fourth implantation site region 296 for the same cardiac cycle as in FIG. 13 are depicted in FIG. 14. As shown, the maximum peak-to-peak values for the first implantation site region 293, the second implantation site region 294, the third implantation site region 295, and the fourth implantation site region 296 are 7 millivolts (mV), 0.5 mV, 5.3 mV, and 5.4 mV, respectively. A threshold value may be selected to be a minimum value such as, e.g., 1 mV.

The exemplary method 300 may increase the scar risk score for a particular implantation site region by one 358 if the implantation site region's peak-to-peak amplitude is less than the threshold value 356 (e.g., 1 mV). In the example depicted in FIG. 14, only the second implantation site region 294 has a peak-to-peak amplitude less than 1 mV, and thus, the scar risk score for only the second implantation site region 294 is increased by one 358.

Additionally, the surrogate electrical activation data for each implantation site region may be evaluated using other metrics that may indicate scar risk such as, e.g., fractionations, ST segment elevation, etc. If the other metrics indicate scar risk (e.g., such as inclusion of fractions and/or ST segment elevations), the process 356 may increase the scar risk score for the particular site by one 358. As shown in FIG. 14, the second implantation site region 294 indicates both fractionations and ST segment elevation, and thus, the scar risk score for the second implantation site region 294 is increased by one 358.

The exemplary method 350 may then update the scar risk score 360 for each of the candidate site regions. The scar risk score, or other metrics related to scarring, may be evaluated by any other methods and/or processes described herein such as, e.g., exemplary method 300 in process 308. As described herein, the second and third implantation site regions 294, 295 were selected as candidate sites in process 306 of exemplary method 300. Since the scar risk for the second implantation site region 294 is higher (e.g., the scar risk score for the second implantation site region 294 is one, which may be indicative of scar) than the scar risk score for the third implantation site region 295 (e.g., the scar risk score for the third implantation site region 295 is zero), the third implantation site region 295 may be identified, or selected, 310 as a target site region in the exemplary method 300. As described herein, after a target site region has been identified 310, a user may then navigate an implantable electrode to the target site region 312 (e.g., in this example, the user may navigate an implantable electrode to the third implantation site region 295).

The implantable electrodes that may be implanted using the exemplary systems, methods, and graphical user interfaces described herein may be part of an implantable medical device (IMD) and/or located on one or more leads configured to be located proximate one or more portions of a patient's heart. For example, the exemplary systems, methods and processes may be used by an exemplary therapy system 10 described herein with reference to FIGS. 15-17.

Figure 15:
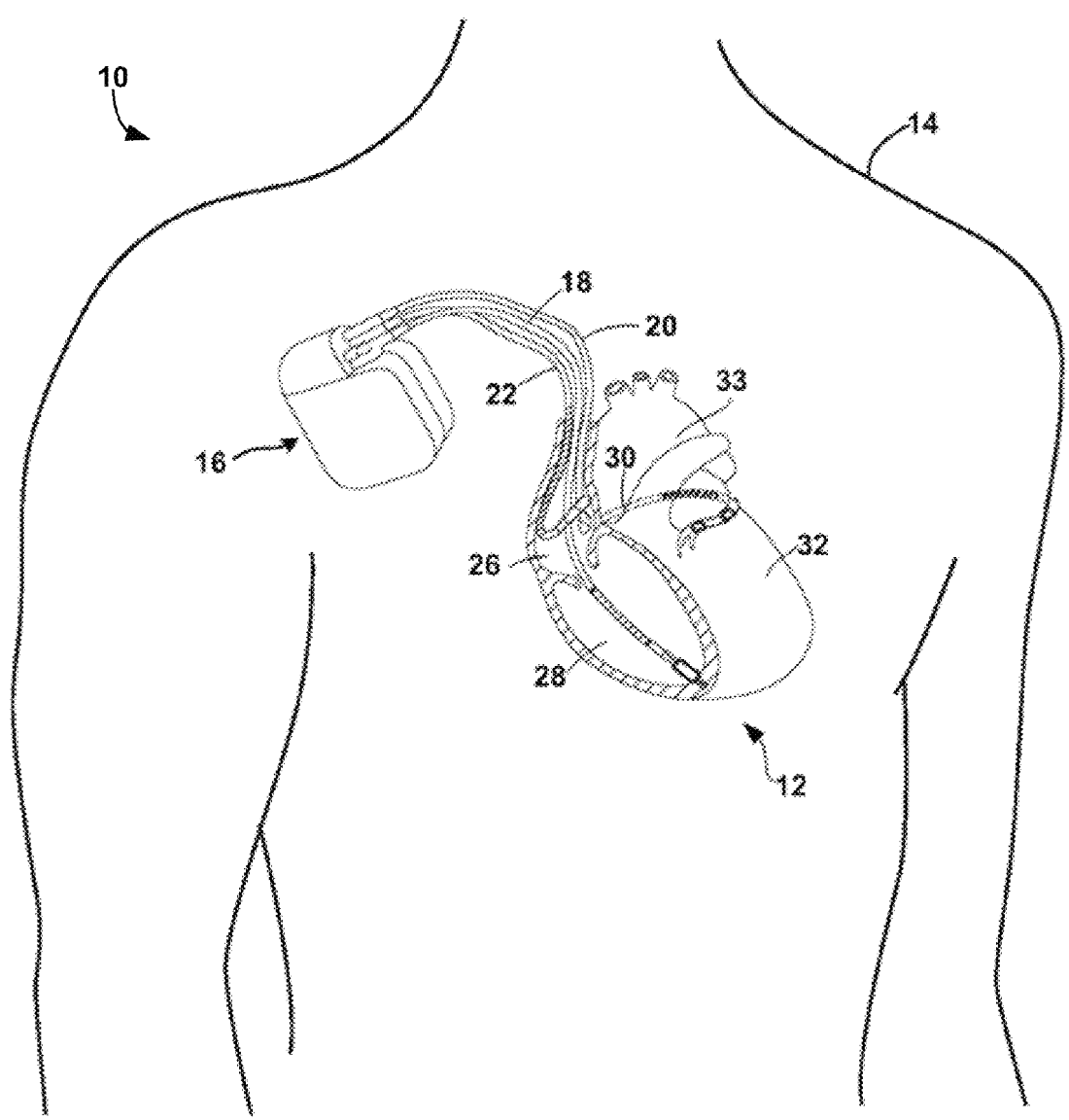
FIG. 15 is a diagram of an exemplary system including an exemplary implantable medical device (IMD).

FIG. 15 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that provides electrical signals to the heart 12 of the patient 14 via electrodes coupled to one or more of the leads 18, 20, 22 (e.g., electrodes that may be implanted in accordance with the description herein, such as, with use of non-invasive selection of implantation site regions).

The leads 18, 20, 22 extend into the heart 12 of the patient 14 to sense electrical activity of the heart 12 and/or to deliver electrical stimulation to the heart 12. In the example shown in FIG. 15, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 16A:
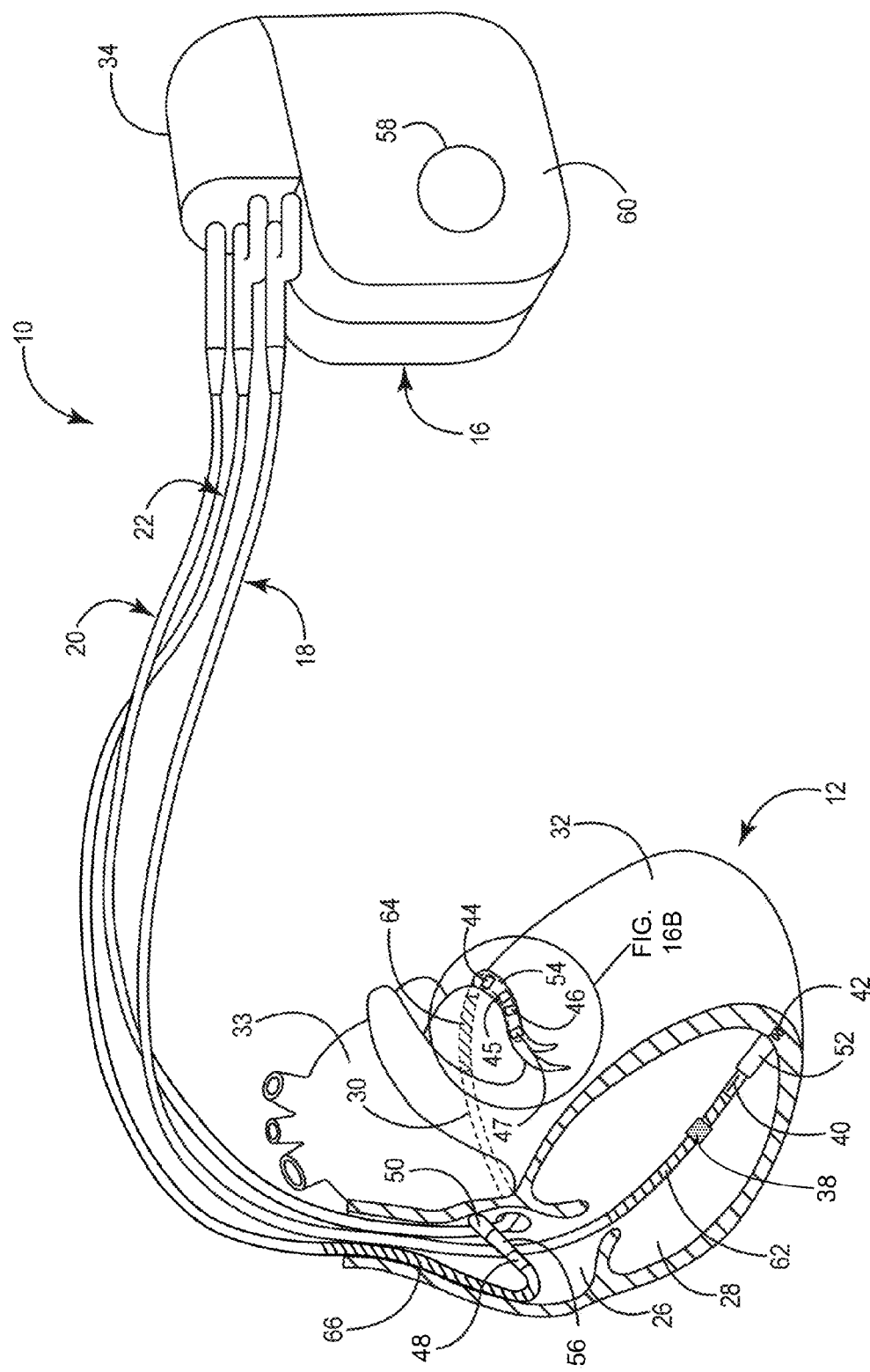
FIG. 16A is a diagram of the exemplary IMD of FIG. 15.
Figure 16B:
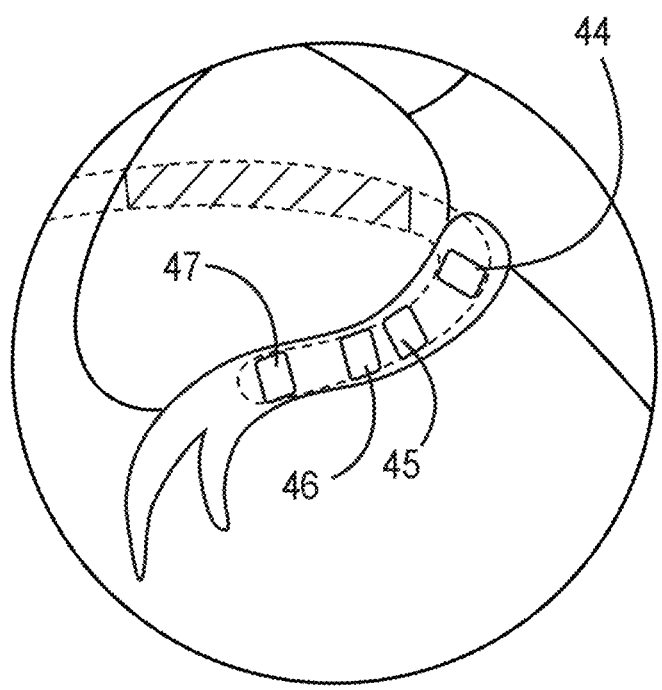
FIG. 16B is a diagram of an enlarged view of a distal end of the electrical lead disposed in the left ventricle of FIG. 16A.

FIG. 16A-16B are conceptual diagrams illustrating the IMD 16 and the leads 18, 20, 22 of therapy system 10 of FIG. 15 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to determine which of the electrodes 40, 42, 44, 45, 46, 47, 48, 50 are the most effective in improving cardiac function. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 16A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIG. 16A, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

The configuration of the exemplary therapy system 10 illustrated in FIGS. 15-17 is merely one example. In other examples, the therapy system may include epicardial leads and/or patch electrodes instead of or in addition to the transvenous leads 18, 20, 22 illustrated in FIG. 15. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 15-17. Still further, other therapy systems may include a single lead that extends from the IMD 16 into the right atrium 26 or the right ventricle 28, or two leads that extend into a respective one of the right atrium 26 and the right ventricle 28.

Figure 17A:
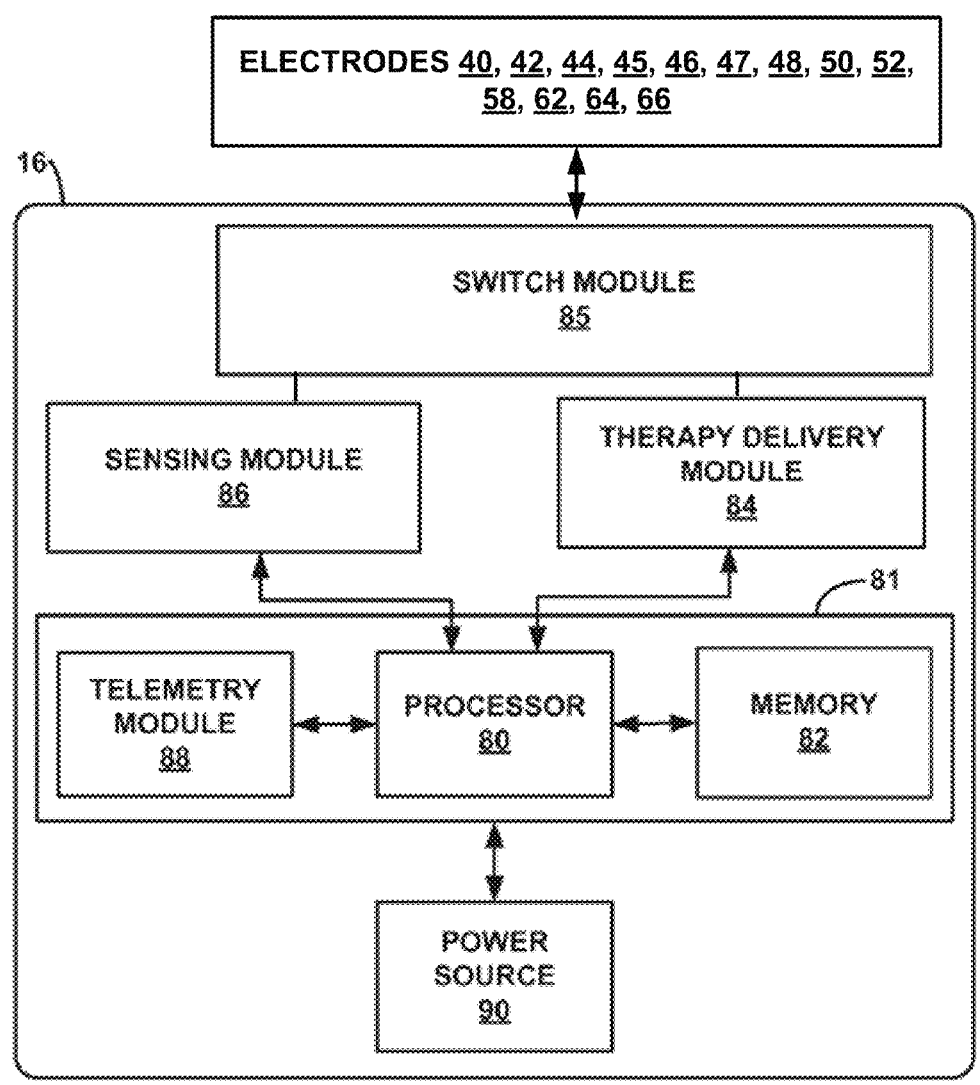
FIG. 17A is a block diagram of an exemplary IMD, e.g., the IMD of FIGS. 15-16.

FIG. 17A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 42 and 50 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 17B:
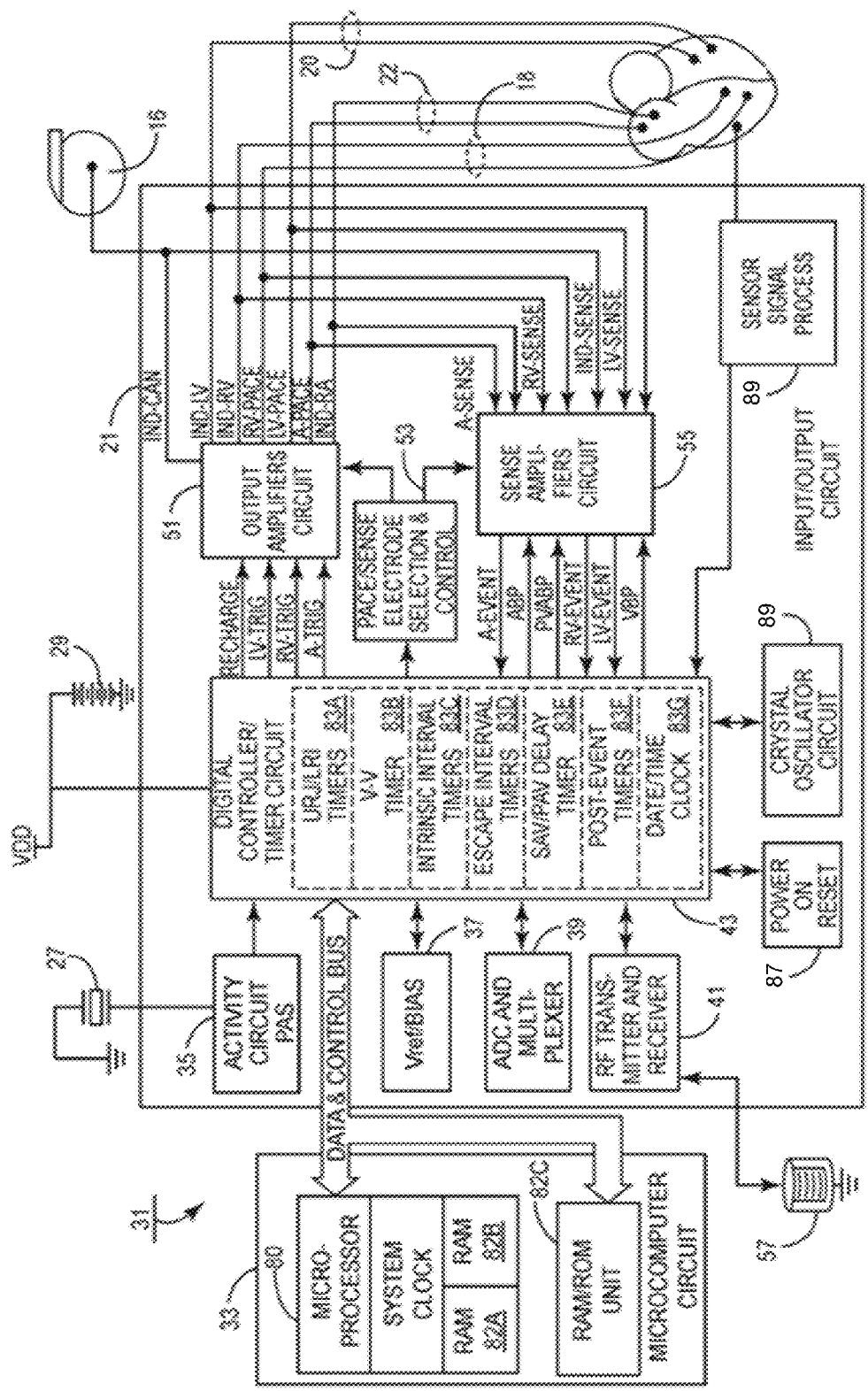
FIG. 17B is another block diagram of an exemplary IMD (e.g., an implantable pulse generator) circuitry and associated leads employed in the system of FIGS. 15-16 for providing three sensing channels and corresponding pacing channels.

FIG. 17B is another embodiment of a functional block diagram for IMD 16. FIG. 17B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which are incorporated herein by reference in their entireties. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A system for assisting in noninvasive location selection for an implantable electrode comprising:
    electrode apparatus comprising a plurality of external electrodes configured to be located proximate tissue of a patient;
    imaging apparatus configured to image at least a portion of blood vessel anatomy of the patient's heart;
    a display apparatus comprising a graphical user interface, wherein the graphical user interface is configured to depict the at least a portion of blood vessel anatomy of the patient's heart for implantation of an implantable electrode; and
    computing apparatus coupled to the electrode apparatus, imaging apparatus, and display apparatus and configured to provide an automated recommendation engine to assist a user in noninvasively selecting a location for the implantable electrode, wherein the computing apparatus is further configured to:
        measure mechanical motion of a plurality of implantation site regions of the at least a portion of blood vessel anatomy of the patient's heart using the imaging apparatus,
        automatically identify one or more identified site regions of the plurality of implantation site regions of the at least a portion of blood vessel anatomy of the patient's heart for implantation of the implantable electrode based on the measured mechanical motion, wherein the one or more identified site regions comprise mechanical motion contraction times greater than or equal to a mechanical motion threshold based on the latest mechanical motion contraction time of the plurality of implantation site regions,
        noninvasively measure surrogate electrical activation time of the one or more of identified site regions of the patient's heart using the plurality of external electrodes of the electrode apparatus, wherein the surrogate electrical activation time for each region of the one or more of identified site regions is noninvasively measured using one or more external electrodes without use of an implantable electrode,
        automatically determine one or more candidate site regions of the one or more of identified site regions of the at least a portion of blood vessel anatomy of the patient's heart for implantation of the implantable electrode based on the measured electrical activation time of the one or more of identified site regions, wherein the one or more candidate site regions comprise electrical activation times greater than or equal to an electrical activation threshold based on the latest electrical activation time of the one or more of identified site regions, and
        identify, on the graphical user interface, the one or more candidate site regions for implantation of the implantable electrode.

2. The system of claim 1, wherein, to measure surrogate electrical activation time of the one or more of identified site regions of the patient's heart using the plurality of external electrodes of the electrode apparatus, the computing apparatus is configured to measure surrogate electrical activation time of each region using one or more external electrodes of the plurality of electrodes proximate to the identified site region for which the surrogate electrical activation time is being measured.

3. The system of claim 1, wherein, to measure surrogate electrical activation time of the one or more identified site regions of the patient's heart using the plurality of electrodes of the electrode apparatus, the computing apparatus is further configured to:
    determine positions of the plurality of external electrodes with respect to the one or more identified site regions of the at least a portion of blood vessel anatomy of the patient's heart using the imaging apparatus;
    associate one or more external electrodes with each region of the one or more identified site regions of the at least a portion of blood vessel anatomy of the patient's heart; and
    measure surrogate electrical activation time of each region of the one or more identified site regions of the at least a portion of blood vessel anatomy of the patient's heart using the one or more external electrodes associated therewith.

4. The system of claim 1, wherein one or more external electrodes of the plurality of external electrodes are associated with each region of the plurality of implantation site regions, wherein the plurality of external electrodes are configured to be positioned proximate tissue of the patient by a user, wherein the one or more external electrodes associated with each region of the plurality of implantation site regions are configured be positioned proximate an area of the patient associated with the respective region of the plurality of implantation site regions,
wherein, to measure surrogate electrical activation time of the one or more identified site regions of the patient's heart using the plurality of electrodes of the electrode apparatus, the computing apparatus is further configured to measure surrogate electrical activation time of each region of the one or more identified site regions of the at least a portion of blood vessel anatomy of the patient's heart using the one or more external electrodes associated therewith.

5. The system of claim 1, wherein the mechanical motion threshold is a selected percentage of the latest mechanical motion contraction time of the plurality of implantation site regions and the electrical activation threshold is a selected percentage of the latest electrical activation time of the one or more identified site regions.

6. The system of claim 1, wherein the computing apparatus is further configured to:
determine a scar risk score for each region of the one or more candidate site regions; and
identify, on the graphical user interface, at least one target site region of the one or more candidate site regions based on the scar risk score for implantation of the implantable electrode.

7. The system of claim 6, wherein the scar risk score is based on at least one of peak-to-peak amplitude of measured mechanical motion of the candidate site region, fractionations of the electrical activity of the candidate site region measured using the one or more electrodes used to measure the surrogate electrical activation time therefor, ST segment elevation of the electrical activity of the candidate site region measured using the one or more electrodes used to measure the surrogate electrical activation time therefor, and low peak-to-peak amplitude of the electrical activity of the candidate site region measured using the one or more electrodes used to measure the surrogate electrical activation time therefor.

8. The system of claim 1, wherein the at least a portion of blood vessel anatomy of the patient's heart comprises at least a portion of the coronary sinus.

9. The system of claim 1, wherein the plurality of external electrodes comprises surface electrodes positioned in an array configured to be located proximate the skin of the patient.

10. A method for assisting in noninvasive location selection for an implantable electrode using an automated recommendation engine comprising:
measuring mechanical motion of a plurality of implantation site regions of at least a portion of blood vessel anatomy of the patient's heart using imaging apparatus;
automatically identifying one or more identified site regions of the plurality of implantation site regions of the at least a portion of blood vessel anatomy of the patient's heart for implantation of the implantable electrode based on the measured mechanical motion, wherein the one or more identified site regions comprise mechanical motion contraction times greater than or equal to mechanical motion threshold based on the latest mechanical motion contraction time of the plurality of implantation site regions,
noninvasively measuring surrogate electrical activation time of the one or more identified site regions of the patient's heart using a plurality of external electrodes, wherein the surrogate electrical activation time for each region of the one or more identified site regions is noninvasively measured using one or more external electrodes without use of an implantable electrode;
automatically determining one or more candidate site regions of the one or more identified site regions of the at least a portion of blood vessel anatomy of the patient's heart for implantation of an implantable electrode based on measured electrical activation time of the one or more identified site regions, wherein the one or more candidate site regions comprise electrical activation times greater than or equal to an electrical activation threshold based on the latest electrical activation time of the one or more identified site regions;
identifying, on a graphical user interface, the one or more candidate site regions for implantation of the implantable electrode; and
navigating at least one implantable electrode to at least one of the identified one or more candidate site regions using the graphical user interface.

11. The method of claim 10, wherein measuring surrogate electrical activation time of the one or more identified site regions of the patient's heart using the plurality of external electrodes comprises measuring surrogate electrical activation time of each identified site region using one or more external electrodes proximate thereto.

12. The method of claim 10, wherein measuring surrogate electrical activation time of the one or more identified site regions of the patient's heart using the plurality of external electrodes comprises:
determining positions of the plurality of external electrodes with respect to the one or more identified site regions of the at least a portion of blood vessel anatomy of the patient's heart using the imaging apparatus;
associating one or more external electrodes with each region of the one or more identified site regions of the at least a portion of blood vessel anatomy of the patient's heart; and
measuring surrogate electrical activation time of each region of the one or more identified site regions of the at least a portion of blood vessel anatomy of the patient's heart using the one or more external electrodes associated therewith.

13. The method of claim 10, wherein one or more external electrodes of the plurality of external electrodes are associated with each region of the plurality of implantation site regions, wherein measuring surrogate electrical activation time of the one or more identified site regions of the patient's heart using the plurality of external electrodes comprises:
positioning the plurality of external electrodes proximate tissue of the patient, wherein the one or more external electrodes associated with each region of the plurality of implantation site regions are positioned proximate an area of the patient associated with the respective region of the plurality of implantation site regions,
wherein, to measure surrogate electrical activation time of the one or more identified site regions of the patient's heart using the plurality of electrodes of the electrode apparatus, the computing apparatus is further configured to measure surrogate electrical activation time of each region of the one or more identified site regions of the at least a portion of blood vessel anatomy of the patient's heart using the one or more external electrodes associated therewith.

14. The method of claim 10, wherein the mechanical motion threshold is a selected percentage of the latest mechanical motion contraction time of the plurality of implantation site regions and the electrical activation threshold is a selected percentage of the latest electrical activation time of the one or more identified site regions.

15. The method of claim 10, wherein the method further comprises:
determining a scar risk score for each region of the one or more candidate site regions;
identifying, on the graphical user interface, at least one target site region of the one or more candidate site regions based on the scar risk score for implantation of the implantable electrode; and
navigating at least one implantable electrode to the at least one identified target site regions using the graphical user interface.

16. The method of claim 15, wherein the scar risk score is based on at least one of peak-to-peak amplitude of measured mechanical motion of the candidate site region, fractionations of the electrical activity of the candidate site region measured using the one or more electrodes used to measure the surrogate electrical activation time therefor, ST segment elevation of the electrical activity of the candidate site region measured using the one or more electrodes used to measure the surrogate electrical activation time therefor, and low peak-to-peak amplitude of the electrical activity of the candidate site region measured using the one or more electrodes used to measure the surrogate electrical activation time therefor.

17. The method of claim 10, wherein the at least a portion of blood vessel anatomy of the patient's heart comprises at least a portion of the coronary sinus.

18. The method of claim 10, wherein the plurality of external electrodes comprises surface electrodes positioned in an array configured to be located proximate the skin of the patient.

19. A system for assisting in noninvasive location selection for an implantable electrode comprising:
electrode apparatus comprising a plurality of external electrodes configured to be located proximate tissue of a patient;
imaging apparatus configured to image at least a portion of blood vessel anatomy of the patient's heart;
a display apparatus comprising a graphical user interface, wherein the graphical user interface is configured to depict the at least a portion of blood vessel anatomy of the patient's heart for implantation of an implantable electrode; and
computing apparatus coupled to the electrode apparatus, imaging apparatus, and display apparatus and configured to provide an automated recommendation engine to assist a user in noninvasively selecting a location for the implantable electrode, wherein the computing apparatus is further configured to:
measure mechanical motion of a plurality of implantation site regions of the at least a portion of blood vessel anatomy of the patient's heart using the imaging apparatus,
automatically identify a plurality of identified site regions of the plurality of implantation site regions of the at least a portion of blood vessel anatomy of the patient's heart for implantation of the implantable electrode based on the measured mechanical motion,
noninvasively measure surrogate electrical activation time of the plurality of identified site regions of the patient's heart using the plurality of external electrodes of the electrode apparatus, wherein the surrogate electrical activation time for each region of the plurality of identified site regions is noninvasively measured using one or more external electrodes without use of an implantable electrode,
automatically determine one or more candidate site regions of the plurality of identified site regions of the at least a portion of blood vessel anatomy of the patient's heart for implantation of the implantable electrode based on the measured electrical activation time of the plurality of identified site regions,
determine a scar risk score for each region of the one or more candidate site regions, and
automatically identify, on the graphical user interface, at least one target site region of the one or more candidate site regions based on the scar risk score for implantation of the implantable electrode.

20. The system of claim 19, wherein, to measure surrogate electrical activation time of the plurality of identified site regions of the patient's heart using the plurality of external electrodes of the electrode apparatus, the computing apparatus is configured to measured surrogate electrical activation time of each identified site region using one or more external electrodes proximate thereto.

21. The system of claim 19, wherein, to measure surrogate electrical activation time of the plurality of identified site regions of the patient's heart using the plurality of electrodes of the electrode apparatus, the computing apparatus is further configured to:
determine positions of the plurality of external electrodes with respect to the plurality of identified site regions of the at least a portion of blood vessel anatomy of the patient's heart using the imaging apparatus;
associate one or more external electrodes with each region of the plurality of identified site regions of the at least a portion of blood vessel anatomy of the patient's heart; and
measure surrogate electrical activation time of each region of the plurality of identified site regions of the at least a portion of blood vessel anatomy of the patient's heart using the one or more external electrodes associated therewith.

22. The system of claim 19, wherein one or more external electrodes of the plurality of external electrodes are associated with each region of the plurality of implantation site regions, wherein the plurality of external electrodes are configured to be positioned proximate tissue of the patient by a user, wherein the one or more external electrodes associated with each region of the plurality of implantation site regions are configured be positioned proximate an area of the patient associated with the respective region of the plurality of implantation site regions,
wherein, to measure surrogate electrical activation time of the plurality of identified site regions of the patient's heart using the plurality of electrodes of the electrode apparatus, the computing apparatus is further configured to measure surrogate electrical activation time of each region of the plurality of identified site regions of the at least a portion of blood vessel anatomy of the patient's heart using the one or more external electrodes associated therewith.

23. The system of claim 19, wherein the scar risk score is based on at least one of peak-to-peak amplitude of measured mechanical motion of the candidate site region, fractionations of the electrical activity of the candidate site region measured using the one or more electrodes used to measure the surrogate electrical activation time therefor, ST segment elevation of the electrical activity of the candidate site region measured using the one or more electrodes used to measure the surrogate electrical activation time therefor, and low peak-to-peak amplitude of the electrical activity of the candidate site region measured using the one or more electrodes used to measure the surrogate electrical activation time therefor.

24. The system of claim 19, wherein the one or more identified site regions comprise mechanical motion contraction times greater than or equal to a mechanical motion threshold based on the latest mechanical motion contraction time of the plurality of implantation site regions and wherein the one or more candidate site regions comprise electrical activation times greater than or equal to an electrical activation threshold based on the latest electrical activation time of the plurality of identified site regions.

25. The system of claim 19, wherein the at least a portion of blood vessel anatomy of the patient's heart comprises at least a portion of the coronary sinus.

26. The system of claim 19, wherein the plurality of external electrodes comprises surface electrodes positioned in an array configured to be located proximate the skin of the patient.

27. A method for assisting in noninvasive location selection for an implantable electrode using an automated recommendation engine comprising:
   measuring mechanical motion of a plurality of implantation site regions of at least a portion of blood vessel anatomy of the patient's heart using imaging apparatus;
   automatically identifying a plurality of identified site regions of the plurality of implantation site regions of the at least a portion of blood vessel anatomy of the patient's heart for implantation of the implantable electrode based on the measured mechanical motion;
   noninvasively measuring surrogate electrical activation time of the plurality of identified site regions of the patient's heart using a plurality of external electrodes, wherein the surrogate electrical activation time for each region of the plurality of identified site regions is noninvasively measured using one or more external electrodes without use of an implantable electrode;
   automatically determining one or more candidate site regions of the plurality of identified site regions of the at least a portion of blood vessel anatomy of the patient's heart for implantation of an implantable electrode based on the measured electrical activation time of the plurality of identified site regions;
   determining a scar risk score for each region of the one or more candidate site regions;
   automatically identifying, on the graphical user interface, at least one target site region of the one or more candidate site regions based on the scar risk score for implantation of the implantable electrode; and
   navigating at least one implantable electrode to at least one of the identified one or more target site regions using the graphical user interface.

28. The method of claim 27, wherein measuring surrogate electrical activation time of the plurality of identified site regions of the patient's heart using the plurality of external electrodes comprises measuring surrogate electrical activation time of each identified site region using one or more external electrodes proximate thereto.

29. The method of claim 27, wherein measuring surrogate electrical activation time of the plurality of identified site regions of the patient's heart using the plurality of external electrodes comprises:
   determining positions of the plurality of external electrodes with respect to the plurality of identified site regions of the at least a portion of blood vessel anatomy of the patient's heart using the imaging apparatus;
   associating one or more external electrodes with each region of the plurality of identified site regions of the at least a portion of blood vessel anatomy of the patient's heart; and
   measuring surrogate electrical activation time of each region of the plurality of identified site regions of the at least a portion of blood vessel anatomy of the patient's heart using the one or more external electrodes associated therewith.

30. The method of claim 27, wherein one or more external electrodes of the plurality of external electrodes are associated with each region of the plurality of implantation site regions, wherein measuring surrogate electrical activation time of the plurality of identified site regions of the patient's heart using the plurality of external electrodes comprises:
   positioning the plurality of external electrodes proximate tissue of the patient, wherein the one or more external electrodes associated with each region of the plurality of implantation site regions are positioned proximate an area of the patient associated with the respective region of the plurality of implantation site regions, and
   measuring surrogate electrical activation time of each region of the plurality of identified site regions of the at least a portion of blood vessel anatomy of the patient's heart using the one or more external electrodes associated therewith.

31. The method of claim 27, wherein the plurality of identified site regions comprise mechanical motion contraction times greater than or equal to a mechanical motion threshold based on the latest mechanical motion contraction time of the plurality of implantation site regions and wherein the one or more candidate site regions comprise electrical activation times greater than or equal to an electrical activation threshold based on the latest electrical activation time of the plurality of identified site regions, wherein the mechanical motion threshold is a selected percentage of the latest mechanical motion contraction time of the plurality of implantation site regions and the electrical activation threshold is a selected percentage of the latest electrical activation time of the plurality of identified site regions.

32. The method of claim 27, wherein the scar risk score is based on at least one of peak-to-peak amplitude of measured mechanical motion of the candidate site region, fractionations of the electrical activity of the candidate site region measured using the one or more electrodes used to measure the surrogate electrical activation time therefor, ST segment elevation of the electrical activity of the candidate site region measured using the one or more electrodes used to measure the surrogate electrical activation time therefor, and low peak-to-peak amplitude of the electrical activity of the candidate site region measured using the one or more electrodes used to measure the surrogate electrical activation time therefor.

33. The method of claim 27, wherein the plurality of identified site regions comprise mechanical motion contraction times greater than or equal to a mechanical motion threshold based on the latest mechanical motion contraction time of the plurality of implantation site regions and wherein the one or more candidate site regions comprise electrical activation times greater than or equal to an electrical activation threshold based on the latest electrical activation time of the plurality of identified site regions.

34. The method of claim 27, wherein the at least a portion of blood vessel anatomy of the patient's heart comprises at least a portion of the coronary sinus.

35. The method of claim 27, wherein the plurality of external electrodes comprises surface electrodes positioned in an array configured to be located proximate the skin of the patient.

36. A system for assisting in noninvasive location selection for an implantable electrode comprising:
- electrode apparatus comprising a plurality of external electrodes configured to be located proximate tissue of a patient;
- imaging apparatus configured to image at least a portion of blood vessel anatomy of the patient's heart;
- a display apparatus comprising a graphical user interface, wherein the graphical user interface is configured to depict the at least a portion of blood vessel anatomy of the patient's heart for implantation of an implantable electrode; and
- computing apparatus coupled to the electrode apparatus, imaging apparatus, and display apparatus and configured to provide an automated recommendation engine to assist a user in noninvasively selecting a location for the implantable electrode, wherein the computing apparatus is further configured to:
    - measure mechanical motion of a plurality of implantation site regions of the at least a portion of blood vessel anatomy of the patient's heart using the imaging apparatus,
    - automatically identify a plurality of identified site regions of the plurality of implantation site regions of the at least a portion of blood vessel anatomy of the patient's heart for implantation of the implantable electrode based on the measured mechanical motion,
    - noninvasively measure surrogate electrical activation time of the plurality of identified site regions of the patient's heart using the plurality of external electrodes of the electrode apparatus, wherein the surrogate electrical activation time for each region of the plurality of identified site regions is noninvasively measured using one or more external electrodes without use of an implantable electrode, and
    - automatically determine one or more candidate site regions of the plurality of identified site regions of the at least a portion of blood vessel anatomy of the patient's heart for implantation of the implantable electrode based on the measured electrical activation time of the plurality of identified site regions.

37. A method for assisting in noninvasive location selection for an implantable electrode using an automated recommendation engine comprising:
- measuring mechanical motion of a plurality of implantation site regions of at least a portion of blood vessel anatomy of the patient's heart using imaging apparatus;
- automatically identifying a plurality of identified site regions of the plurality of implantation site regions of the at least a portion of blood vessel anatomy of the patient's heart for implantation of the implantable electrode based on the measured mechanical motion,
- noninvasively measuring surrogate electrical activation time of the plurality of identified site regions of the patient's heart using a plurality of external electrodes, wherein the surrogate electrical activation time for each region of the plurality of identified site regions is noninvasively measured using one or more external electrodes without use of an implantable electrode; and
- automatically determining one or more candidate site regions of the plurality of identified site regions of the at least a portion of blood vessel anatomy of the patient's heart for implantation of an implantable electrode based on the measured surrogate electrical activation time of the plurality of identified site regions.

* * * * *